US011890357B2

(12) United States Patent
Low et al.

(10) Patent No.: US 11,890,357 B2
(45) Date of Patent: *Feb. 6, 2024

(54) FIBROBLAST ACTIVATION PROTEIN (FAP) TARGETED IMAGING AND THERAPY IN FIBROSIS

(71) Applicant: Purdue Research Foundation, West Lafayette, IN (US)

(72) Inventors: Philip Stewart Low, West Lafayette, IN (US); Suraj U. Hettiarachchi, West Lafayette, IN (US); Yen-Hsing Li, West Lafayette, IN (US); Jyoti Roy, North Bethesda, MD (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/809,810

(22) Filed: Jun. 29, 2022

(65) Prior Publication Data

US 2023/0033291 A1  Feb. 2, 2023

Related U.S. Application Data

(63) Continuation of application No. 17/285,717, filed as application No. PCT/US2019/056257 on Oct. 15, 2019, now Pat. No. 11,426,472.

(60) Provisional application No. 62/861,028, filed on Jun. 13, 2019, provisional application No. 62/746,822, filed on Oct. 17, 2018.

(51) Int. Cl.
*A61K 51/04* (2006.01)
*A61K 47/54* (2017.01)
*A61K 31/4709* (2006.01)
*A61K 49/00* (2006.01)

(52) U.S. Cl.
CPC ...... *A61K 51/0482* (2013.01); *A61K 31/4709* (2013.01); *A61K 47/545* (2017.08); *A61K 49/0043* (2013.01)

(58) Field of Classification Search
CPC .. G01N 33/582; G01N 33/6893; G01N 33/60; G01N 33/532; A61K 49/0052; A61K 51/0455; A61K 49/0032; A61K 49/0043; A61K 47/545; A61P 11/00; C09B 57/00; C09B 59/004
See application file for complete search history.

(56) References Cited

U.S. PATENT DOCUMENTS

| 9,346,814 | B2 | 5/2016 | Jansen et al. |
| 11,426,472 | B2 | 8/2022 | Low et al. |
| 2011/0092504 | A1 | 4/2011 | Bo et al. |
| 2012/0294930 | A1 | 11/2012 | Ren et al. |
| 2016/0168118 | A1 | 6/2016 | Zhu et al. |
| 2019/0015531 | A1 | 1/2019 | Babich et al. |
| 2021/0121584 | A1 | 4/2021 | Babich et al. |
| 2021/0128757 | A1 | 5/2021 | Babich et al. |
| 2022/0001037 | A1 | 1/2022 | Low et al. |

FOREIGN PATENT DOCUMENTS

| AU | 2019360944 | | 1/2023 |
| CN | 112912731 | A | 6/2021 |
| EP | 2804859 | B1 | 6/2019 |
| EP | 3867648 | A | 6/2022 |
| JP | 2022-505171 | A | 1/2022 |
| JP | 7161044 | | 10/2022 |
| JP | 2022191399 | | 12/2022 |
| WO | WO-2013107820 | A1 | 7/2013 |
| WO | WO-2015192123 | A1 | 12/2015 |
| WO | WO-2018111989 | A1 | 6/2018 |
| WO | WO-2018187631 | A1 | 10/2018 |
| WO | WO-2019083990 | A2 | 5/2019 |
| WO | WO-2020081522 | A1 | 4/2020 |
| WO | WO-2021207682 | A2 | 10/2021 |

OTHER PUBLICATIONS

"Australian Application Serial No. 2022224743, Voluntary Amendment filed Jan. 18, 2023", 17 pgs.
"U.S. Appl. No. 17/285,717, Notice of Allowance dated Apr. 4, 2022", 10 pgs.
"U.S. Appl. No. 17/285,717, Supplemental Preliminary Amendment Filed Mar. 7, 2022", 4 pgs.
"European Application Serial No. 19874435.1, Extended European Search Report dated May 25, 2022", 11 pgs.
"European Application Serial No. 19874435.1, Response to Communication pursuant to Rules 161(2) and 162 EPC filed Nov. 25, 2021", 5 pgs.
"International Application Serial No. PCT/US2019/056257, International Preliminary on Patentability mailed Apr. 29, 2021", 7 pgs.
"International Application Serial No. PCT/US2019/056257, International Search Report mailed Jan. 31, 2020", 4 pgs.
"International Application Serial No. PCT/US2019/056257, Written Opinion dated Jan. 31, 2020", 5 pgs.
Hettiarachchi, S. U., et al., "Targeted inhibition of PI3 kinase/mTOR specifically in fibrotic lung fibroblasts suppresses pulmonary fibrosis in experimental models", Science Translational Medicine. vol. 12.

(Continued)

*Primary Examiner* — Michael G. Hartley
*Assistant Examiner* — Leah H Schlientz
(74) *Attorney, Agent, or Firm* — Schwegman Lundberg & Woessner, P.A.

(57) ABSTRACT

Excessive deposition of extracellular matrix is a hallmark of Idiopathic pulmonary fibrosis (IPF), it is advantageous to target the cells and the mechanisms associated with this process. By targeting myofibroblasts (specialized contractile fibroblasts) that are key for the development of IPF with drugs conjugated with fibroblast activation protein (FAP), this technology helps minimize the production of extracellular matrix in the lungs and provides a new treatment option for patients diagnosed with IPF.

11 Claims, 14 Drawing Sheets

(56) References Cited

OTHER PUBLICATIONS

Janseen, Koen, et al., "Extended Structure-Activity Relationship and Pharmacokinetic Investigation of (4-Quinolinoyl)glycyl-2-cyanopyrrolidine Inhibitors of Fibroblast Activation Protein (FAP)", Journal of Medicinal Chemistry, 57, (2014), 3053-3074.

Knight, S. D., et al., "Discovery of GSK2126458, a Highly Potent Inhibitor of PI3K and the Mammalian Target of Rapamycin", ACS Med. Chem. Lett vol. 1, No. 1, (Apr. 8, 2010), 39-43.

Tsai, Ting-Yueh, et al., "Substituted 4-Carboxymethylpyroglutamic Acid Diamides as Potent and Selective Inhibitors of Fibroblast Activation Protein", J. Med. Chem., 53(18), (2010), 6572-6583.

"U.S. Appl. No. 17/285,717, Supplemental Notice of Allowability dated Jul. 20, 2022", 4 pgs.

"Australian Application Serial No. 2019360944, First Examination Report dated Jul. 11, 2022", 3 pgs.

"Australian Application Serial No. 2019360944, Response filed Sep. 2, 2022 to First Examination Report dated Jul. 11, 2022", 6 pgs.

"Chinese Application Serial No. 201980068239.3, Notice of Passing Preliminary Examination dated May 13, 2021", (w/ English Translation), 2 pgs.

"Japanese Application Serial No. 2021-521113, Notice of Issuance dated Sep. 14, 2022", (w/ English Translation), 5 pgs.

"Japanese Application Serial No. 2021-521113, Notification of Reasons for Refusal dated Aug. 3, 2022", (w/ English Translation), 7 pgs.

"Japanese Application Serial No. 2021-521113, Response filed Aug. 29, 2022 to Notification of Reasons for Refusal dated Aug. 3, 2022", (w/ English Translation of Claims), 15 pgs.

"Japanese Application Serial No. 2021-521113, Voluntary Amendment filed Jul. 11, 2022", (w/ English Translation of Claims), 11 pgs.

"European Application Serial No. 19874435.1, Response filed Dec. 21, 2022 to Extended European Search Report dated May 25, 2022", 11 pgs.

"Chinese Application Serial No. 201980068239.3, Notification to Make Divisional Application dated Aug. 11, 2023", W/O English Translation, 1 page.

"Chinese Application Serial No. 201980068239.3, Office Action dated Jun. 16, 2023", W/O English Translation, 1 page.

"Chinese Application Serial No. 201980068239.3, Response filed Jul. 19, 2023 to Office Action dated Jun. 16, 2023", w/o English claims, 2 pgs.

| | Structure | Docking score | Docking gscore |
|---|---|---|---|
| 1 | 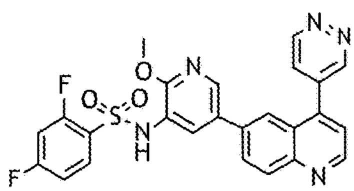 | -8.98 | -9.071 |
| 2 | 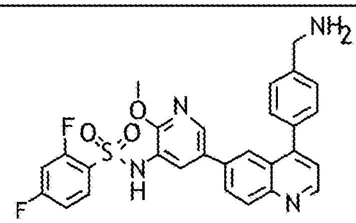 | -8.035 | -10.066 |
| 3 | 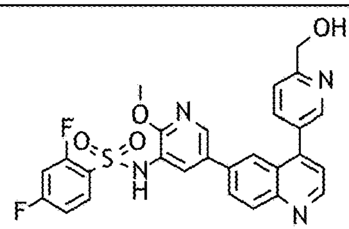 | -10.047 | -10.138 |
| 4 | 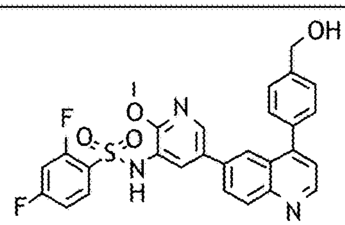 | -7.675 | -9.706 |
| 5 | 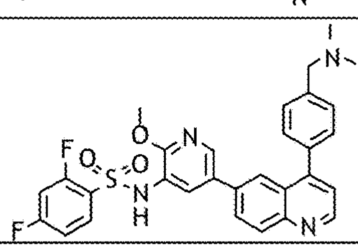 | -8.538 | -8.648 |

FIBROBLAST ACTIVATION PROTEIN (FAP) TARGETED IMAGING AND THERAPY IN FIBROSIS

FIELD OF INVENTION

This disclosure provides a conjugate and method of using thereof to image and/or treat idiopathic pulmonary fibrosis (IPF). Specifically, Fibroblast active protein (FAP) targeted imaging agent or therapeutic drug is delivered to IPF to either guide the diagnosis of IPF or significantly reduces IPF pathological extracellular matrix deposition.

BACKGROUND

Fibrotic diseases constitute a major health problem worldwide affecting a large number of individuals.

Under pathologic circumstances, the normal tissue repair reaction escapes the homeostatic regulatory mechanisms and evolves into an uncontrolled fibrotic process characterized by the progressive over-production of extracellular matrix which disrupts the normal organ architecture and ultimately leads to organ failure.

Virtually every organ in the human body can be affected by physiologic and pathologic fibrotic reactions, but the most commonly affected organs are the lungs, kidneys, liver, skin, heart, and bladder. For example, fibrosis of the liver represents a paradigm for this disease, as it may be reversible at early stages but become irreversible as it progresses to cirrhosis, resulting in liver cancer in addition to end stage disease. It has multiple potentially preventable etiologies; they include HBV and HCV infection, obesity, alcoholism, and aflatoxin among others; each presents opportunities for and serious barriers to primary and/or secondary prevention. For many other fibrotic diseases, the underlying etiologies are less clear, although many are associated with chronic production of proteolytic enzymes, fibrogenic cytokines, growth factors, and angiogenic factors, presumably secondary to triggering irritants (e.g., radiation, chronic infections, toxins). Others are congenital or associated with autoimmunity. For fibrosis of all types, the point of irreversibility and the molecular mechanisms by which it occurs are not well defined. Organ failure is the end-result of uncontrolled fibrosis. Treatment of fibrotic diseases in these organs is necessary to prevent the eventual organ failure and morbidity.

Idiopathic pulmonary fibrosis (IPF) is a progressive fibrotic disease of lungs. It is believed to be caused by repetitive environment injury to the lining of the lungs and resulting abnormal wound-healing responses. When tissues of lung experience prolonged activation of wound healing responses, the result usually is permanent scarring, organ malfunction and more significantly, death.

It is estimated that there are about 128,000 people living with IPF, with 48,000 new cases diagnosed annually in US alone. Among them, about 40,000 IPF patients die each year. Median survival age after diagnosis is approximately 2-3 years. Owing to the widespread and multi-organ occurrence of fibrotic diseases, it is difficult to determine their total incidence, although it has been estimated that as high as 45% of the mortality in Western developed countries is caused by their collective occurrence.

Until recently, there have been no curative therapies for IPF, with treatments options limited to lung rehabilitation and oxygen therapy.

Currently, FDA approved two drugs in 2014 for the treatment of IPF: pirfenidone and nintedanib. However, both drugs show limited and inconsistent efficacy in IPF patients. Very recently, several kinase inhibitors have been introduced into human clinical trials with the hope that they might block essential steps in the fibrotic process, however their on targeted activities against the same enzymes in healthy tissues have raised concerns regarding systemic toxicities.

In more advanced cases, lung transplantation can be a final option, but finding an HLA match is often difficult and avoiding transplant rejection can be challenging.

Therefore, an urgent need for therapies that can slow IPF progression exists.

SUMMARY OF THE INVENTION

This disclosure provides a conjugate to target Fibroblast Activation Protein (FAP) expressing cells in fibrotic lung diseases. The conjugate comprises a targeting ligand to FAP (TL), a linker (L) and an effector (E), wherein the TL has a molecular weight below 10,000, the L is a non-releasable linker when the effector is an imaging agent or a radioactive therapeutic agent; the L is a releasable linker when the effector is a therapeutic drug. The linker is selected from the group consisting of pegylated, alkyl, sugar or peptide based dual linker.

In some preferred embodiment the aforementioned imaging agent is a fluorescent molecule.

In some preferred embodiment the aforementioned conjugate comprises the structure of FAPL-FITC below:

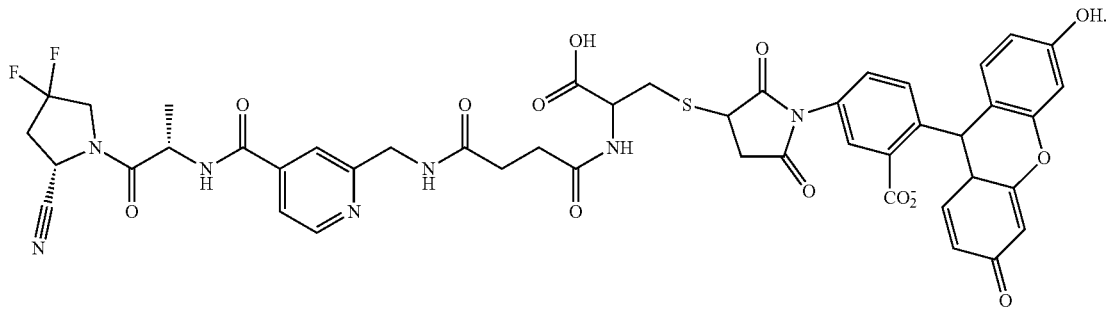

In some preferred embodiment the aforementioned fluorescent dye is a near infrared dye and the conjugate has the structure of
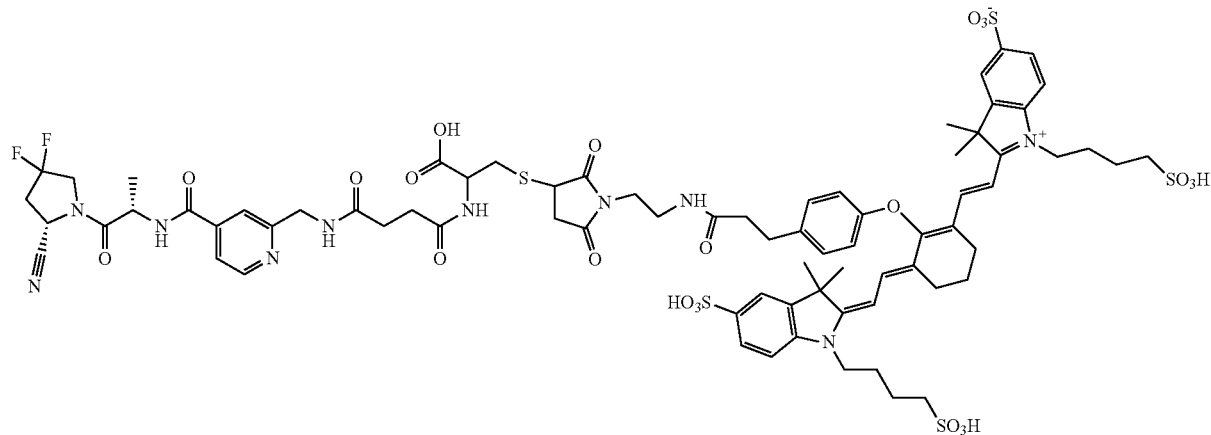
In some preferred embodiment the aforementioned florescent molecule comprising the structure of
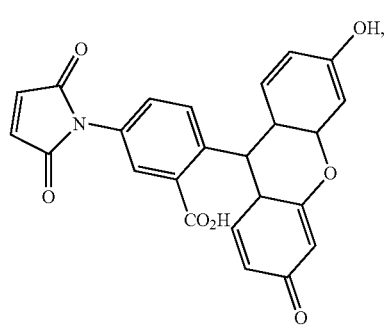
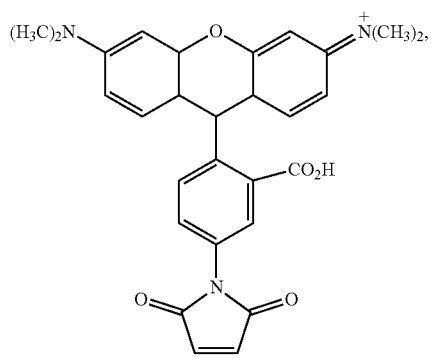
or
-continued
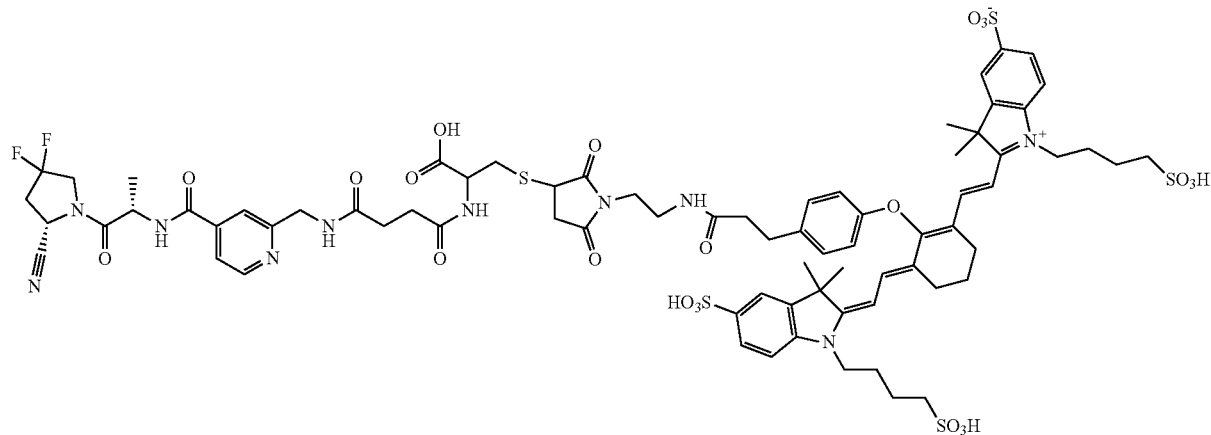
In some preferred embodiment the aforementioned effector is a PET imaging agent.

In some preferred embodiment the aforementioned PET imaging agent comprises the structure of
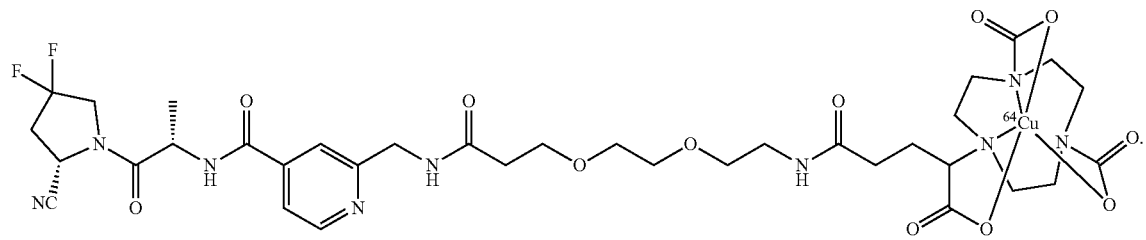
In some preferred embodiment the aforementioned effector is a 99mTc imaging agent comprising a DOTA, NOTA, TETA or NODAGA chelating agent
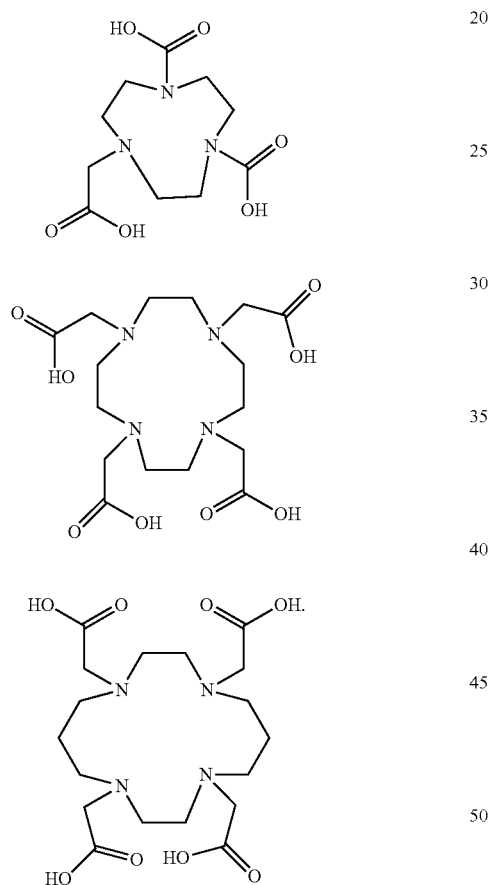
In some preferred embodiment the aforementioned 99mTc imaging agent comprises the structure of.
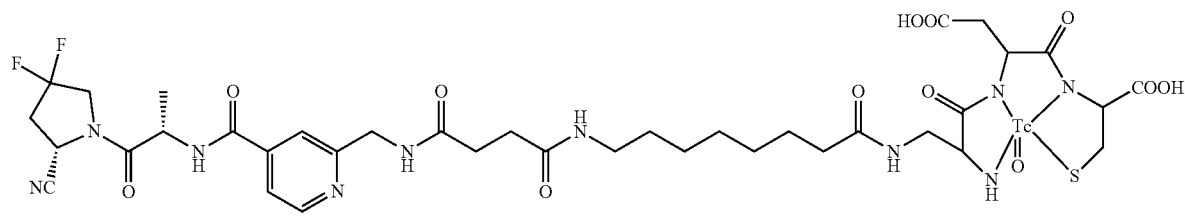

In some preferred embodiment the aforementioned radioactive therapeutic agent contains the structure of

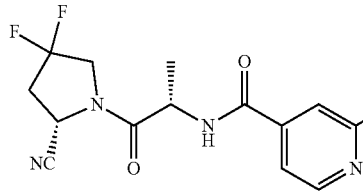

In some preferred embodiment the aforementioned TL is a small molecule comprising the structure of

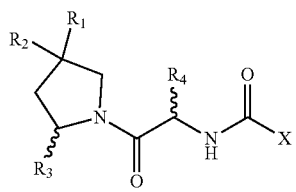

wherein x is

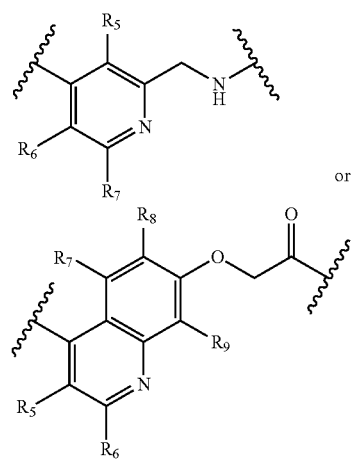

wherein $R_1$ and $R_2$ are the same or different, and are each independently selected from the group consisting of hydrogen, halogen and $C_1$-$C_4$ alkyl;

$R_3$ is a $C_1$-$C_4$ alkyl, nitrile, or isonitrile;

$R_4$ is H or —$CH_3$ $R_5$ and $R_6$ are the same or different, and are each independently selected from the group consisting of hydrogen, halogen, and $C_1$-$C_4$ alkyl, $R_7$-$R_9$ are the same or different, and are each independently selected from the group consisting of hydrogen, methoxy, halogen, $CF_3$ and $C_1$-$C_4$ alkyl In some preferred embodiment the aforementioned $R_1$ and $R_2$ is a halogen.

In some preferred embodiment the aforementioned each of $R_1$ and $R_2$ is fluorine.

In some preferred embodiment the aforementioned effector is a kinase inhibitor for VEGFR1, VEGFR2, VEDFR3, FGFR1, FGFR2, or PDGFR.

In some preferred embodiment the aforementioned effector is a kinase inhibitor for FAK or ROCK.

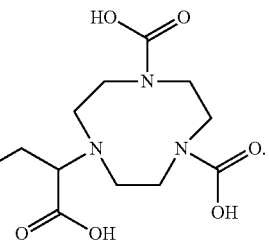

In some preferred embodiment the aforementioned effector is an SMAD inhibitor.

In some preferred embodiment the aforementioned effector is a cytotoxic agent.

In some preferred embodiment the aforementioned effector is a PI-3 kinase inhibitor.

This disclosure further provides a PI-3 Kinase inhibitor comprising the structure of (PI3KI1).

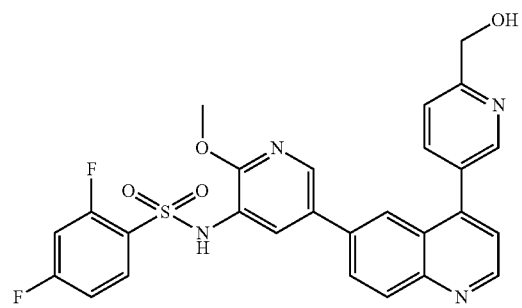 [SMILES: COc1ncc(-c2ccc3nccc(-c4ccc(CO)nc4)c3c2)cc1NS(=O)(=O)c1ccc(F)cc1F]

In some preferred embodiment the aforementioned conjugate having the structure of (FAPL-PI3KI1)

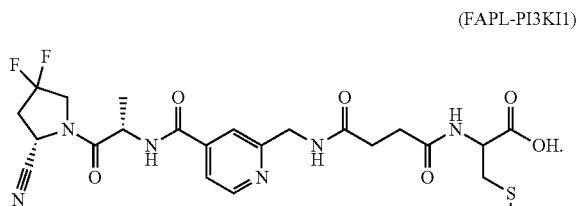

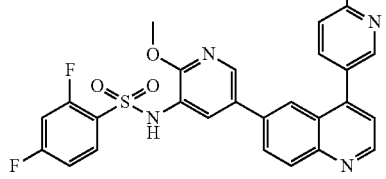

In some preferred embodiment the aforementioned PI-3 kinase inhibitor comprising the structure below:

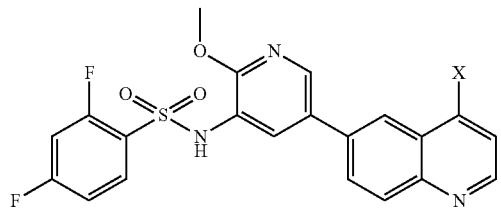

wherein X can be any of the following

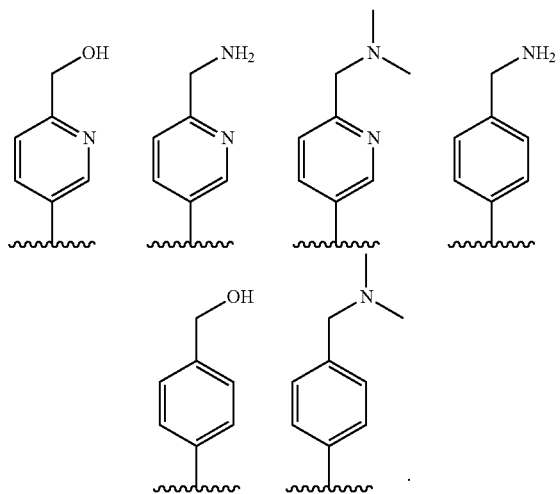

In some preferred embodiment the aforementioned targeting ligand to FAP has a binding affinity to FAP in the range between about 1 nM and about 10 nM.

This disclosure further provides a method of diagnosing IPF in a subject, comprising the following steps:

obtaining the lung tissue from the subject, wherein said tissue may or may not express FAP in fibroblast cells;

providing to the tissue with a conjugate of TL-L-I, wherein TL is a targeting ligand A conjugate to target Fibroblast Activation Protein (FAP) expressing cells in fibrotic lung diseases, wherein said TL has a molecular weight below 10,000, said L is a non-releasable linker, said I is an imaging agent; and identifying imaging illustrated fibroblast cells as FAP expressing activated fibroblast cells as the hallmark of IPF.

In some preferred embodiment the aforementioned TL is a small molecule having the structure of

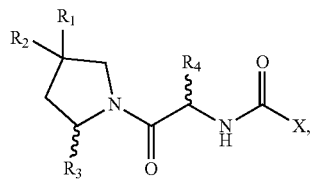

wherein x is

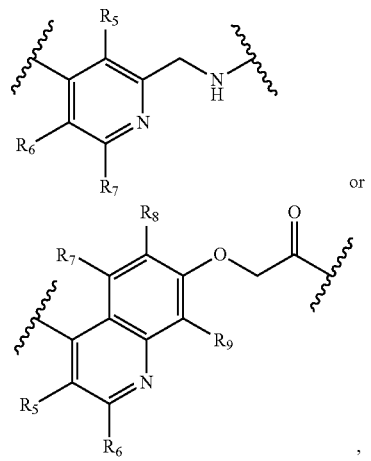

or wherein $R_1$ and $R_2$ are the same or different, and are each independently selected from the group consisting of hydrogen, halogen and $C_1$-$C_4$ alkyl;

$R_3$ is a $C_1$-$C_4$ alkyl, nitrile, or isonitrile;

$R_4$ is H or —$CH_3$;

$R_5$ and $R_6$ are the same or different, and are each independently selected from the group consisting of hydrogen, halogen, and $C_1$-$C_4$ alkyl;

$R_7$-$R_9$ are the same or different, and are each independently selected from the group consisting of hydrogen, methoxy, halogen, $CF_3$ and $C_1$-$C_4$ alkyl.

This disclosure further provides a method of treating IPF in a subject. The method comprising the steps of:

providing to the IPF patient cells with a pharmaceutically effective amount of conjugate of TL-L-D, wherein TL is a targeting ligand to FAP that has a molecular weight below 10,000, L is a releasable linker and D is a therapeutic drug that has pan PI-3Kinase inhibitory effect; and monitoring lung tissue extracellular matrix deposit amount reduction upon the treatment of TL-L-D.

In some preferred embodiment the aforementioned TL is a small molecule having the structure of structure of

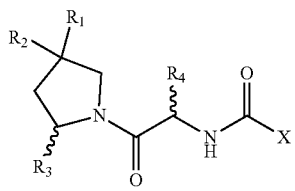

wherein x can be

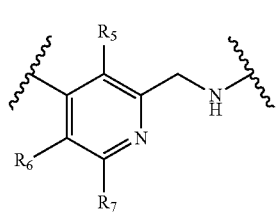

or

-continued

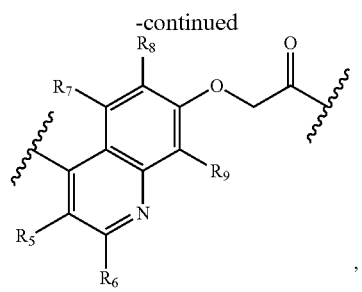

wherein $R_1$ and $R_2$ are the same or different, and are each independently selected from the group consisting of hydrogen, halogen and $C_1$-$C_4$ alkyl;

$R_3$ is a $C_1$-$C_4$ alkyl, nitrile, or isonitrile;

$R_4$ is H or —$CH_3$;

$R_5$ and $R_6$ are the same or different, and are each independently selected from the group consisting of hydrogen, halogen, and $C_1$-$C_4$ alkyl, $R_7$-$R_9$ are the same or different, and are each independently selected from the group consisting of hydrogen, methoxy, halogen, $CF_3$ and $C_1$-$C_4$ alkyl.

In some preferred embodiment the aforementioned D has the structure of following:

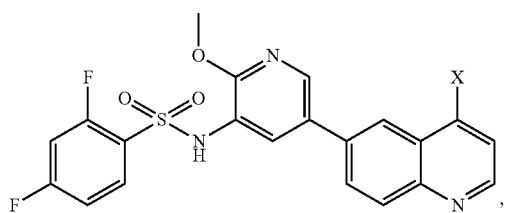

wherein X can be any of the following:

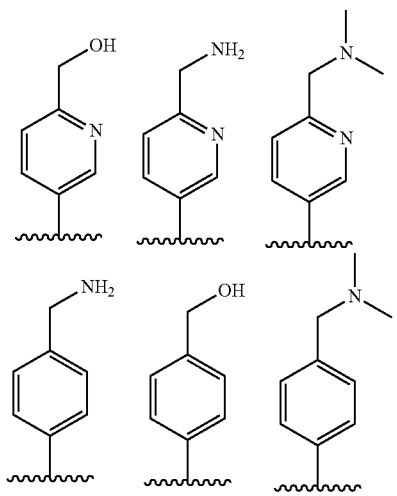

In some preferred embodiment the aforementioned method uses a conjugate that reduces collagen I deposits on activated fibroblast cells.

In some preferred embodiment the aforementioned method uses a subject that is a mouse IPF model induced by intratracheal administration of bleomycin at about 0.75 u/kg for consecutive 10 days.

In some preferred embodiment the aforementioned method administering a conjugate at about 0.2-10 umol/kg to the mouse IPF model for consecutive 10 days and the conjugate is FAPL_PI3KI1 with the structure of.

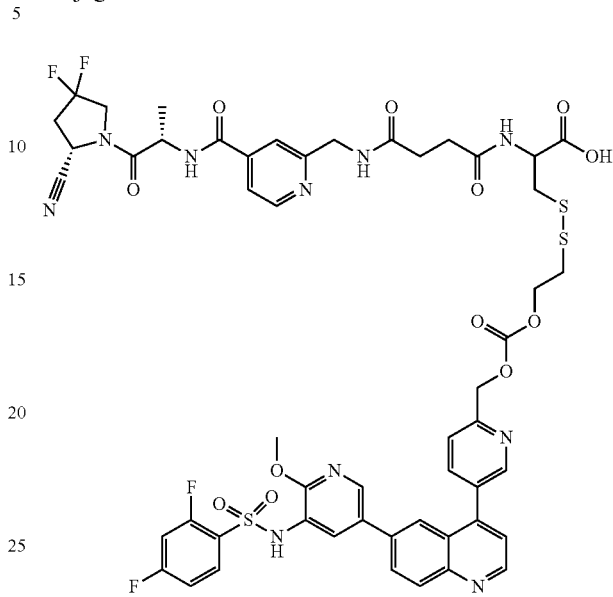

In some preferred embodiment the aforementioned method monitors extracellular matrix collagen I.

In some preferred embodiment the aforementioned method reduces the hydroxyproline production of fibroblast cells.

In some preferred embodiment the aforementioned method uses a subject of a mouse IPF model induced by silica or radiation.

These and other features, aspects and advantages of the present invention will become better understood with reference to the following figures, associated descriptions and claims.

αSMA and FAP predominantly expressed in IPF lung fibroblasts and targeted by FAP-FITC. (A) IPF fibroblasts and non IPF control fibroblast were seeded and stained with antibody against FAP or aSMA. (B) IPF cells were incubated with FAPL-FITC (10 nM) and analyzed by flow cytometry.

Figure 4:
Figure 4:
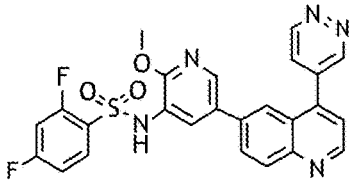
Figure 4:
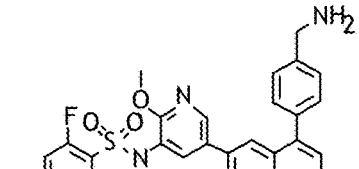
Figure 4:
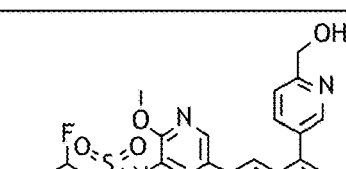
Figure 4:
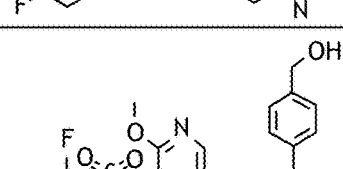
Figure 4:
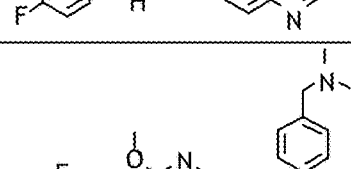
Figure 4C:
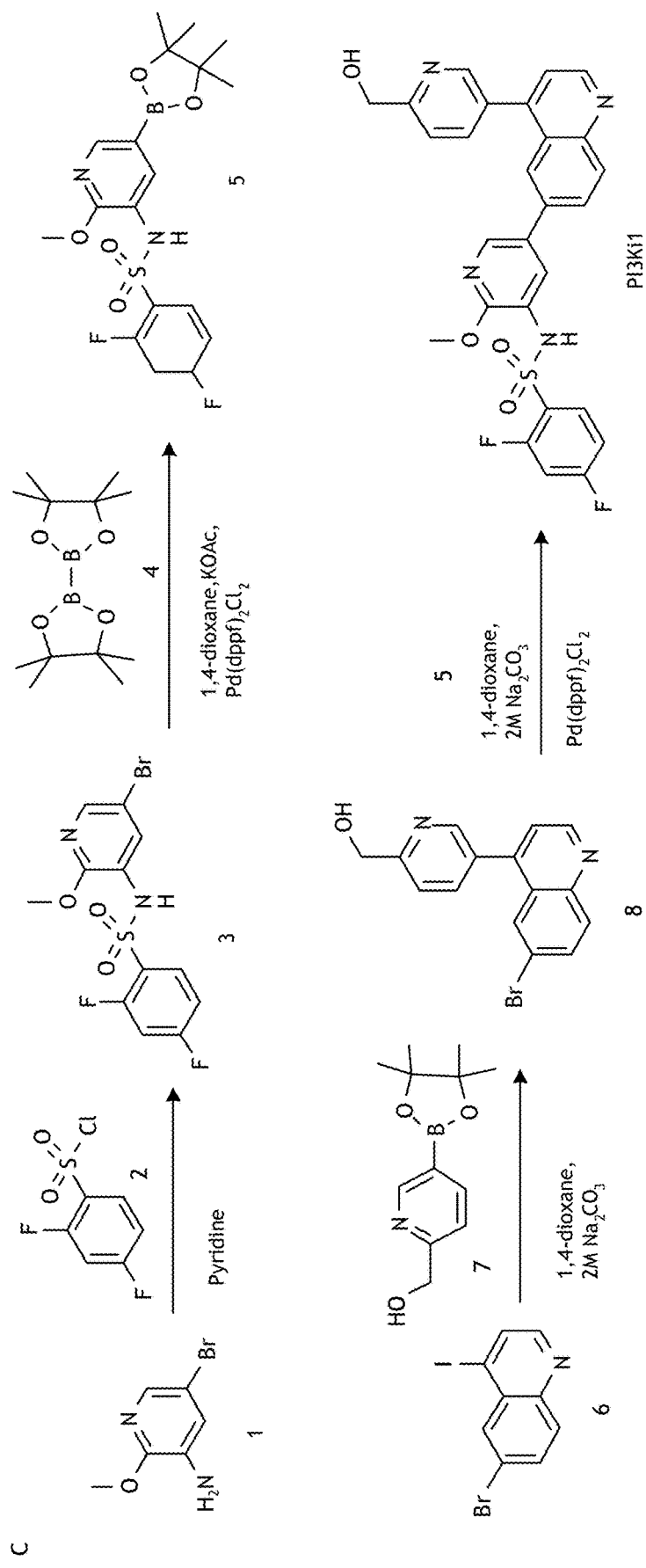

FIG. 4. Design and synthesis of PI3KI1 and FAPL-PI3KI1

Design and the synthesis of a novel pan-Pi3K inhibitor. (A) Putative binding of PI3KI1, based on the crystal structure of Pi3Kg (PDB code: 3L08). (B) docking scores of compounds docked. (C) Synthetic scheme of PI3KI1

Figure 5:
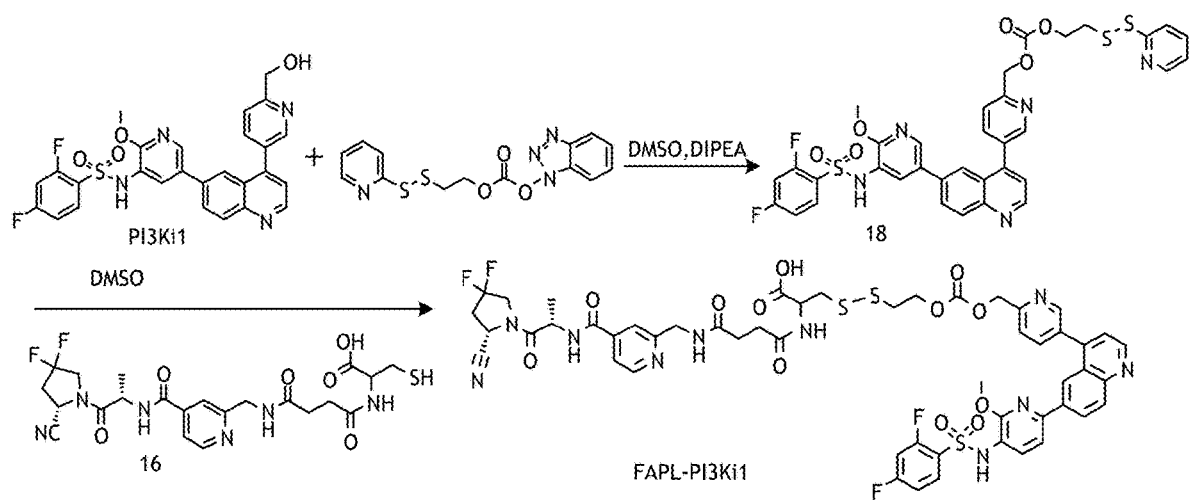
Figure 5:
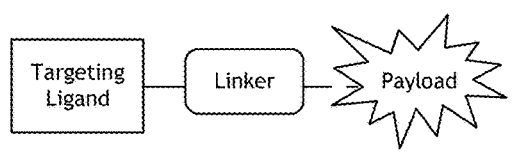

FIG. 5. Synthesis of novel FAP targeted pan-Pi3K inhibitor (FAPL_PI3KI1).

Figure 6:
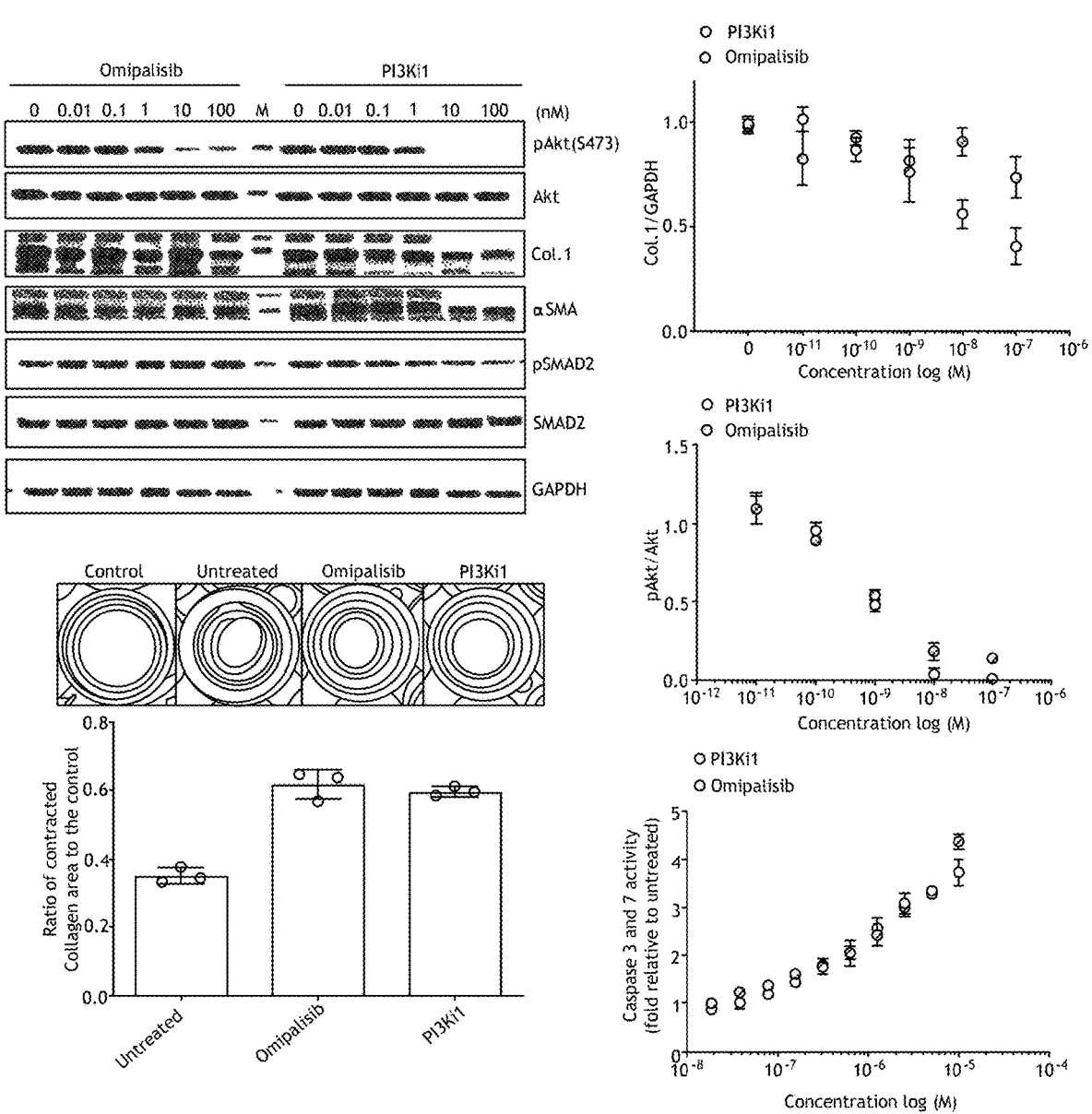

FIG. 6. Evaluation of myofibroblast inactivation with FAP-targeted PI-3 kinase inhibitor in vitro.

PI3KI1 inhibits Akt phosphorylation, proliferation, collagen secretion and collagen gel contraction in HLF-1 fibroblasts. (A) PI3KI1 structure. (B) Confluent HLF-1 fibroblasts were stimulated with TGFβ (1 ng/mL) with indicated PI3KI1 or OMIPALISIB and lysates collected for Western blotting. PI3KI1 inhibits TGF-β (1 ng/ml for 24 hr) induced AKT phosphorylation with $IC_{50}$ 1.4 nM. Collagen 1 and αSMA expression was suppressed by 100 nM PI3KI1, but pSMAD2 was not affected by PI3K inhibitors. (C) MTT assay and Caspase 3 and 7 activity (Supplementary data) show PI3KI1 inhibited HLF-1 proliferation at >100 nM. (D) HLF-1 fibroblasts were stimulated with TGFβ (1 ng/mL) for 3 days and level of secreted collagen in culture medium was determined by Sirius Red staining. (E) PI3KI1 (100 nM for 12 hours) disrupted fibroblasts reorganization and contraction, characteristics of activated fibrosis, by collagen gel contraction assay. Data are analysis by t-test; *p<0.05, **p<0.01.

Figure 7:
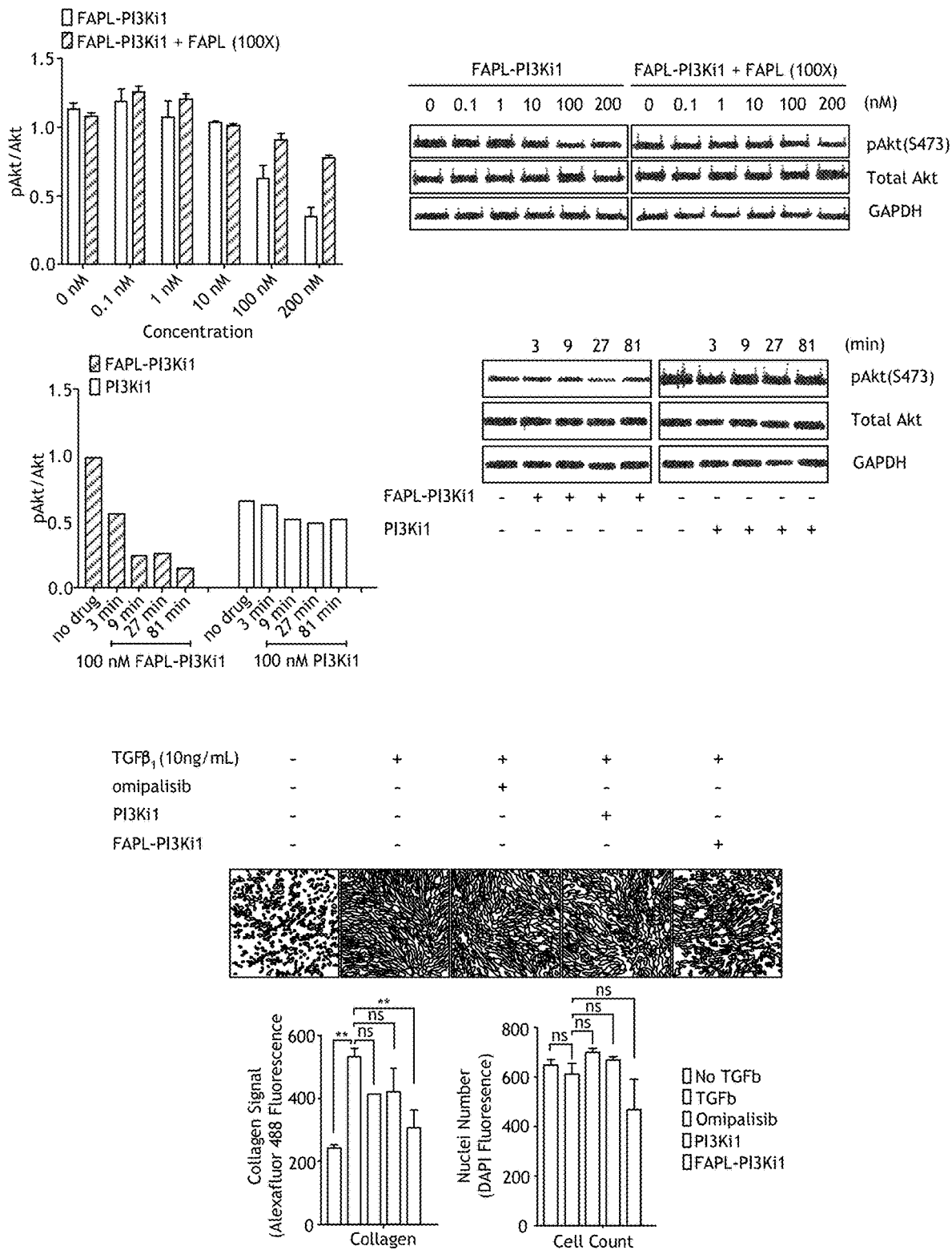

FIG. 7. Ex vivo IPF patient cell line data

PI3KI1 and PI3KI1-FAPL suppressed TGFβ-induced collagen production in IPF fibroblasts. (B) Confluent IPF fibroblasts were stimulated for 48 h with TGFβ (1 ng/mL) with increasing concentrations of OMIPALISIB or PI3KI1 or PI3KI1-FAPL and Collagen I expression was assayed by molecular crowding assay with high content image analysis. Data are expressed as relative fluorescent intensity over TGFβ treated IPF fibroblasts (C) and cell counts obtained from DAPI counterstaining (D).

Figure 8:
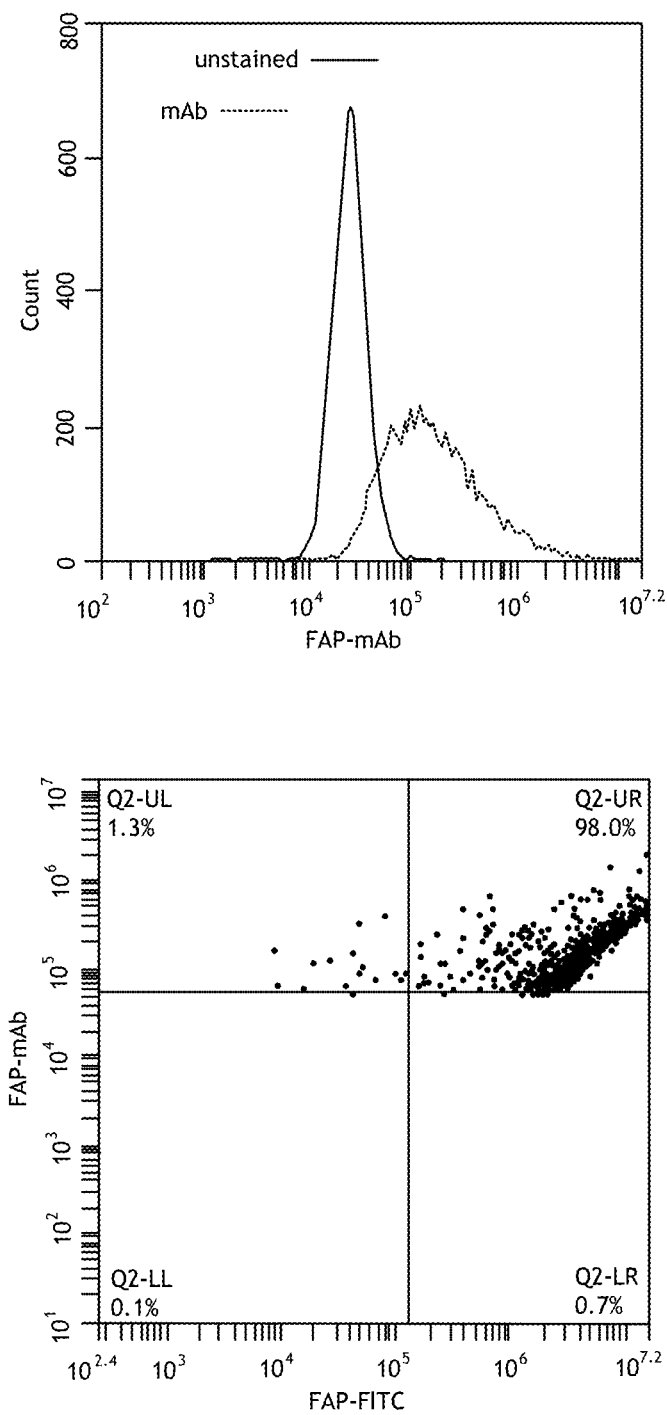

FIG. 8. Evaluation of FAP targeting in mouse fibroblast cell line in vitro

FAPL-FITC targets mouse FAP in mouse fibroblast cells. Fluorescence binding affinity study of FAPL_FITC in HLF-hFAP cells. (C) Binding of FAPL_FITC to TGFb induced mouse NIH-3T3 cell line.

Figure 9:
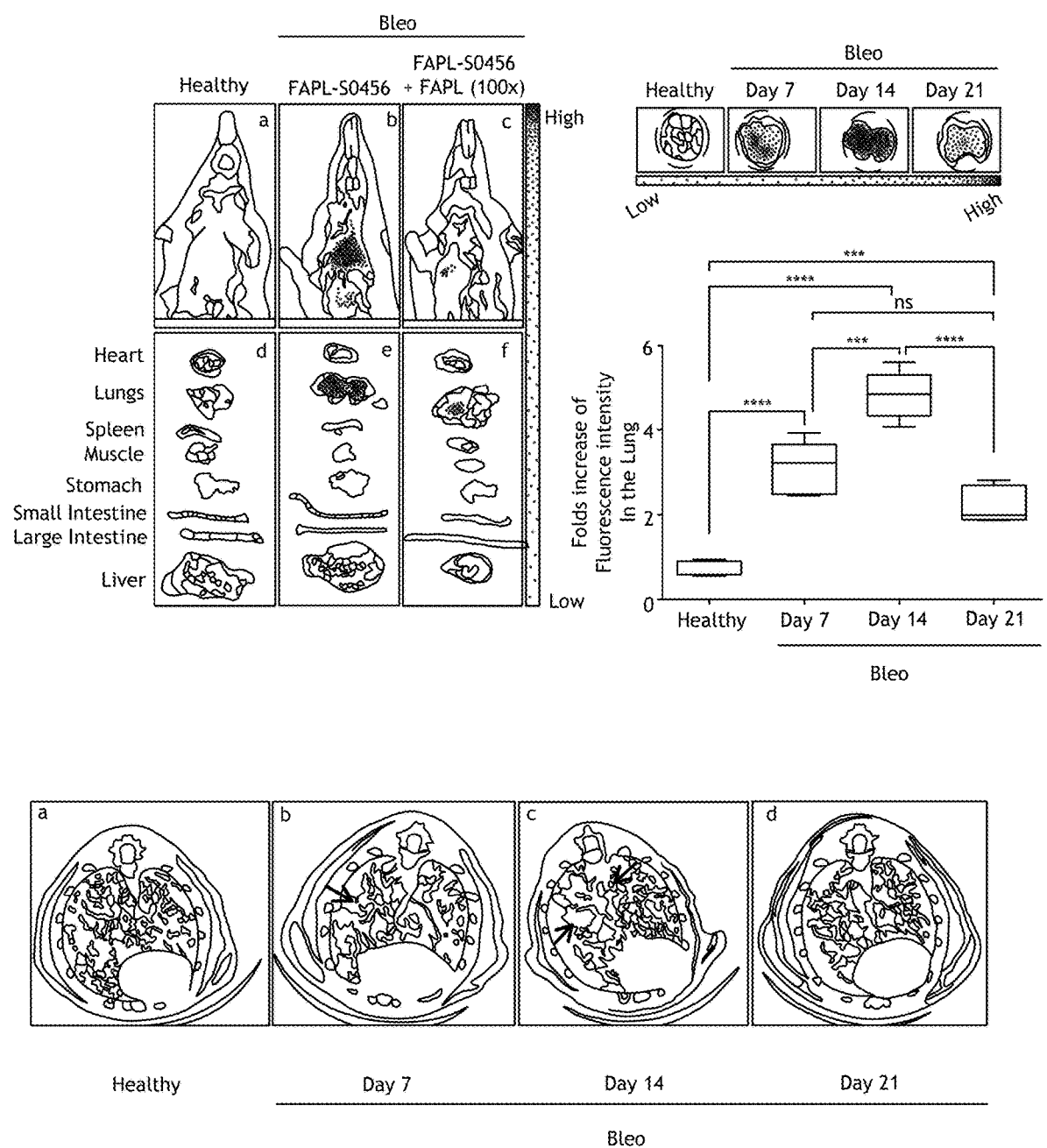

FIG. 9. Evaluation of FAP targeting of IPF lung in mouse model of IPF in vivo (I) Optical imaging of experimental lung fibrosis in mice with FAP-a targeted NIR dye, open body (A), biodistribution (B). Representative optical images in PBS administered (a, d) and bleomycin (0.75 u/Kg) administered mice at day 14 in the presence (b, e) or in the absence (c, f) of 100-fold excess of the FAP ligand. Images were acquired after 4 hours post injection of 5 nmoles of the FAP_S0456. The color bar indicates radiant efficiency (low, 2.7×108; high, 5.9×108). Biodistribution: 1) heart, 2) lung, 3) spleen, 4) muscle, 5) stomach, 6) small intestine, 7) large intestine, 8) liver, and 9) kidneys. (II) Representative optical images of the lungs, with FAP_S0456 of PBS administered healthy control (a), 7 days (b), 14 days (c), and 21 days (d) after bleomycin administration, and Quantitative fluorescence intensity change in the lungs over time. For optical imaging all the images were acquired and compared under the same condition, after 4 hours post injection of 5 nmoles of the FAP_S0456. The color bar indicates radiant efficiency (low, $1.7×10^8$; high, $3.6×10^8$). (III) Representative CT images of the lungs, PBS administered healthy control (a), 7 days (b), 14 days (c), and 21 days (d) after bleomycin administration.

Figure 10:
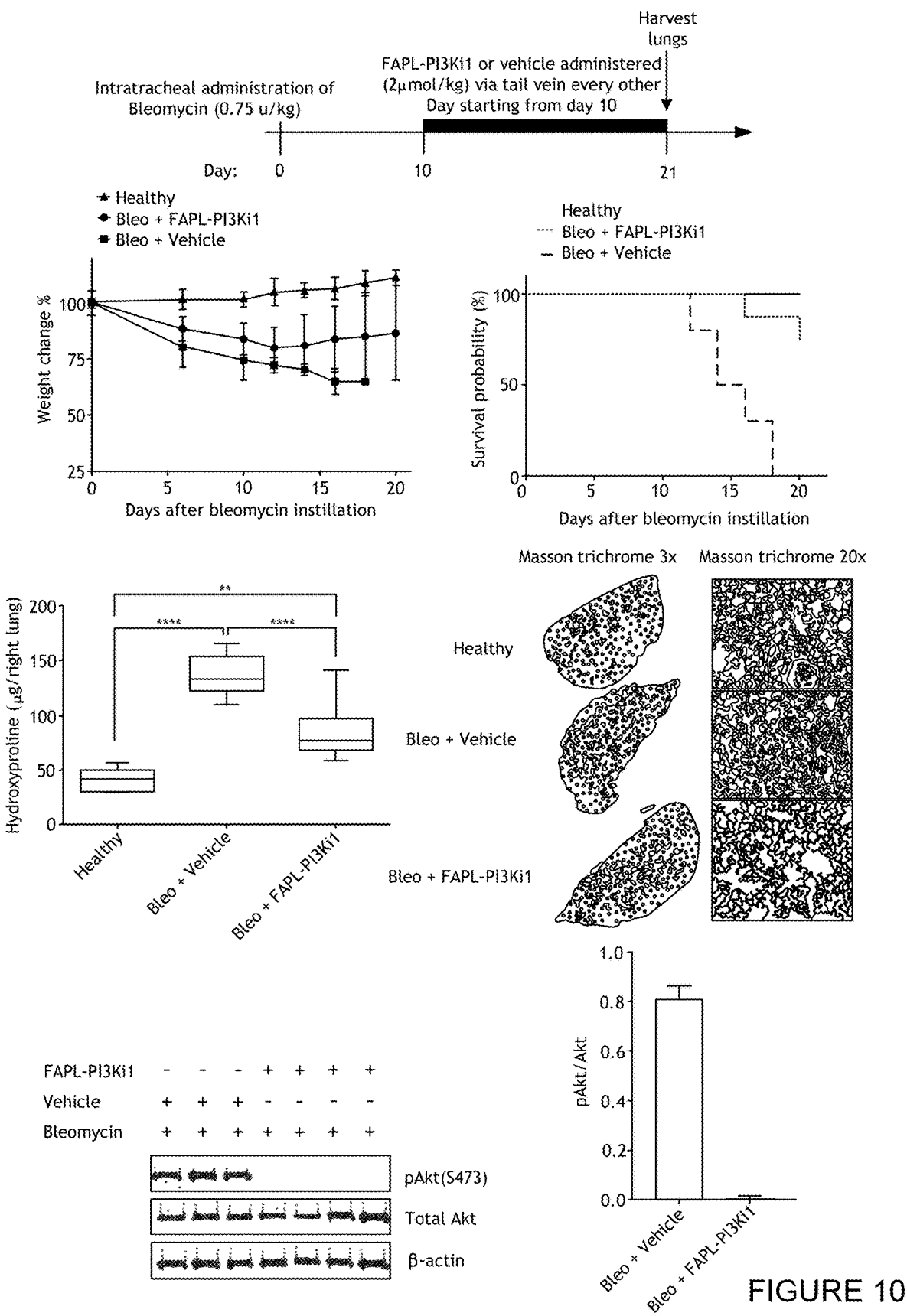
Figure 11:
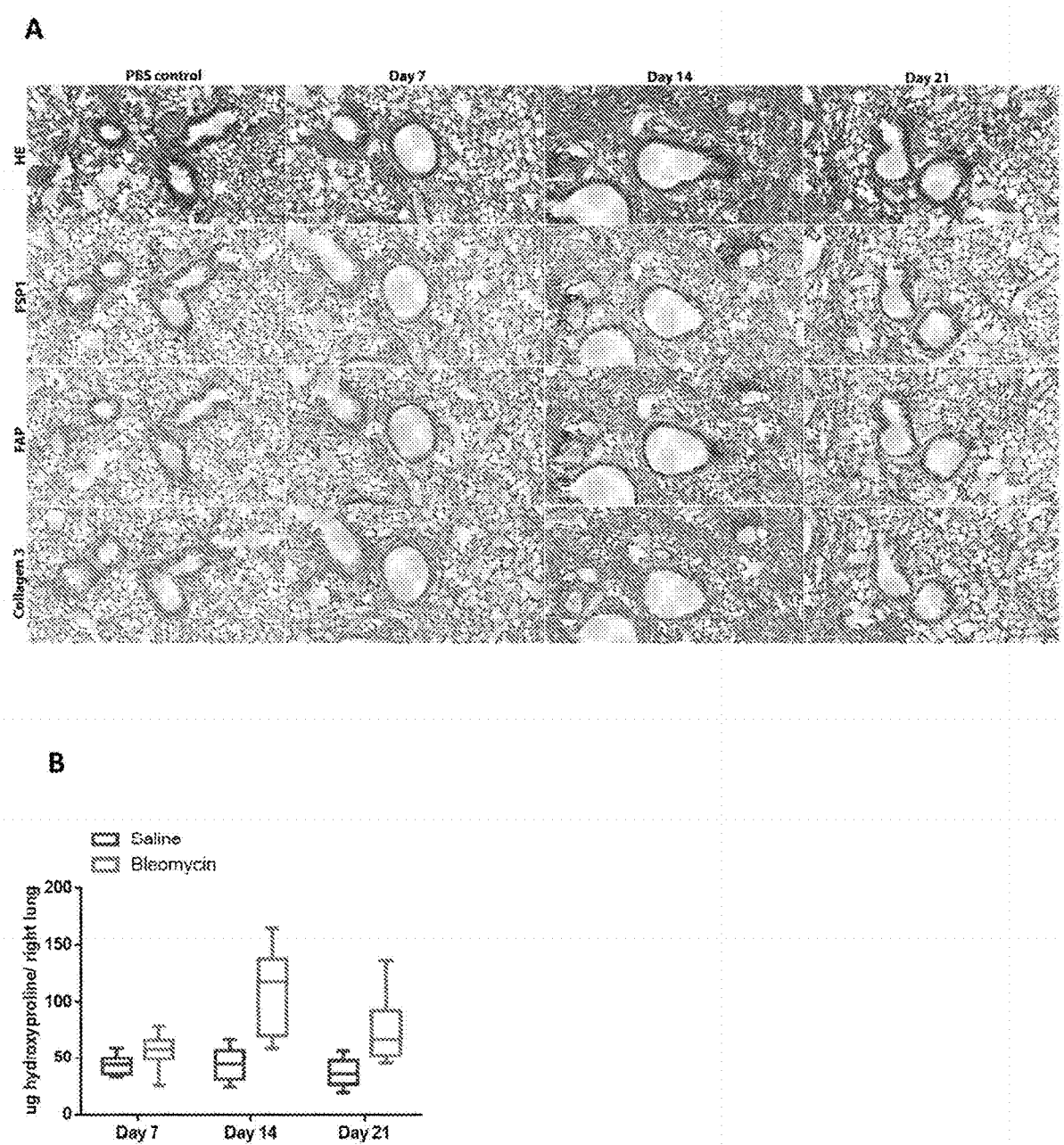

FIG. 10. Evaluation of myofibroblast inactivation with FAPL-targeted PI-3 kinase inhibitor in vivo Therapy with FAP-a targeted Pi3K inhibitor in bleomycin treated mice. (A) Schematic representation of the experimental protocol for induction, treatment and examination of pulmonary fibrosis in a mouse model. (B) Survival probability of the FAPL_PI3KI1 treated mice over the saline control. (C) Hydroxyproline content (ug/lung) of control (saline), bleomycin treated with and without FAPL_PI3KI1 treatment at day 21. (D) Body weight change FIG. 11. Characterization of pulmonary fibrosis in mice over time, post-bleomycin (0.75 u/Kg) administration. (B) Hydroxyproline analysis of disease progression in bleomycin treated mice with saline treated mice at day 7, day 14, and day 21

Figure 12:
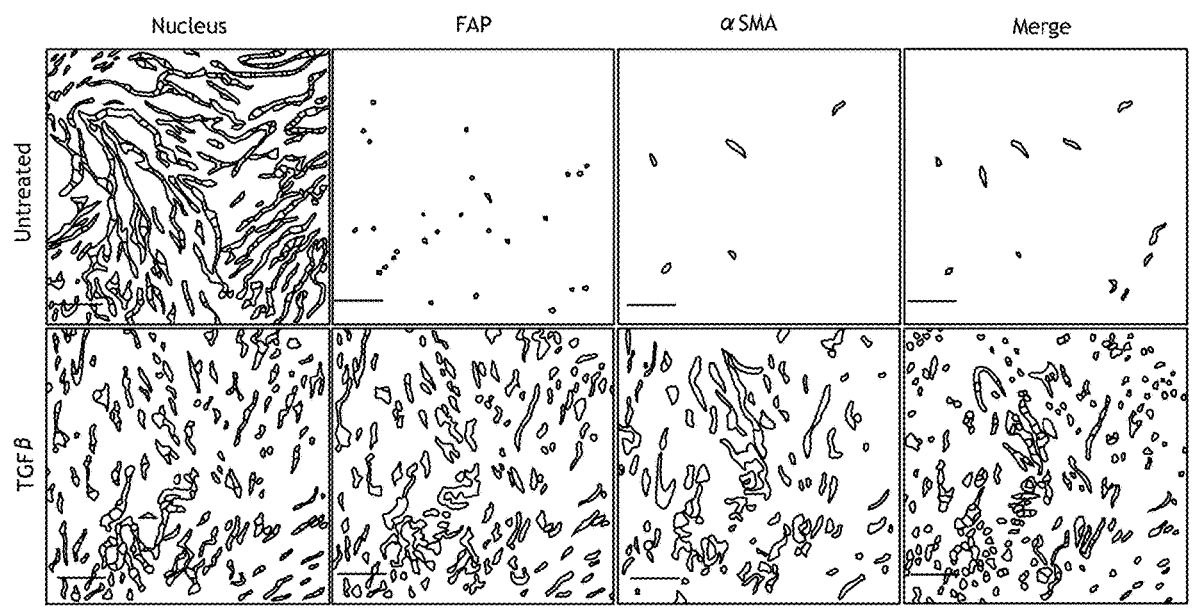

FIG. 12. TGF-β (1 ng/ml for 24 hr) induced FAP and aSMA expression in human lung fibroblast cell line (HLF-1). HLF-1 cells were 0.4% serum starved for 12 hr and then stimulated by TGF-β (1 ng/mL) for 24 hr. FAPL and aSMA expression were detected by immunofluorescence analysis.

FIG. 13. Chemical structure of Compound 3.
FIG. 14. Chemical structure of Compound 8.
FIG. 15. Chemical structure of Compound 5.
FIG. 16. Chemical structure of FAPL_PI3KI1.
FIG. 17. General method of making synthetically derived compounds.
FIG. 18. Caspase 3 and 7 activity show PI3KI1 inhibited HLF-1 proliferation at >100 nM.
FIGS. 19A-19B. Radio-imaging of experimental lung fibrosis in mice with FAP targeted $^{99m}TC$ conjugate. FIG. 19A shows FAP targeted $^{99m}TC$ in various organs, and FIG. 19B shows FAP targeted $^{99m}TC$ in the lungs.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

IPF is a lethal, chronic, progressive disease, and increases with age, particularly in individuals over the age of 50. In US, IPF kills as many people (about 40,000 per year) as breast cancer, with most patients dying within 3-5 years of diagnosis.

Until recently, there have been no curative therapies for IPF, with treatments options limited to lung rehabilitation and oxygen therapy. However, in 2014, two new drugs, pirfenidone and nintedanib, were approved by the FDA for treatment of IPF. Unfortunately, both show limited and inconsistent efficacy, primarily retarding disease progression but not leading to stable resolution of the disease.

Very recently, several kinase inhibitors have been introduced into human clinical trials with the hope that they might block essential steps in the fibrotic process, however their on-target activities against the same enzymes in healthy tissues have raised concerns regarding systemic toxicities.

In more advanced cases, lung transplantation can be a final option, but finding an HLA match is often difficult and avoiding transplant rejection can be challenging.

Given the difficulty of finding an enzyme or pathway that is uniquely required for pathologic fibrosis, we have undertaken to identify a molecular marker that is primarily expressed on fibrosis-producing cells that might be exploited for the targeted delivery of drugs to these cells.

In response to stimulation by activated immune cells such as macrophages and T cells, fibroblasts become activated to myofibroblasts that then accumulate in areas called fibroblast foci where they produce the collagen that causes the fibrosis.

These myofibroblasts are readily distinguished from non-pathologic fibroblasts by their expression of a transmembrane protein, fibroblast activation protein (FAP) that is critical for the process of collagen remodeling.

The unique expression of FAP on myofibroblasts provides a marker that can conceivably be exploited for the targeted delivery of drugs to myofibroblasts.

In this study, a low molecular weight ligand specific for fibroblast activation protein (FAP) was synthesized and evaluated for binding to an FAP-expressing human lung fibroblast cell line transfected with FAP (HLF1-FAP). The potency of a novel PI-3 kinase inhibitor targeted with the FAP ligand (FAPL_PI3KI1) in suppressing collagen synthesis and secretion by both HLF1-hFAP cell line and IPF patient cell lines was also examined. Specific targeting of the fibrotic lungs was then evaluated in vivo using an FAPL-targeted NIR dye (FAP-S0456). Finally, the ability of the targeted inhibitor, FAPL-PI3KI1, to reduce collagen deposition and fibrosis in the lungs of bleomycin-induced mice was assessed.

We have shown that FAP ligand binds to FAP in HLF1-FAP cells with ~3 nM affinity. FAPL-PI3KI1 was observed to potently inhibit collagen secretion/synthesis ($IC_{50}$=<10 nM) in both HLF1-hFAP and IPF patient cell lines. NIR imaging of bleomycin-induced mice showed specific targeting of FAPL-S0456 NIR dye to fibrotic lungs with good competition. In vivo therapy with FAPL-PI3KI1 demonstrated increased survival and decreased hydroxyproline/collagen production compared to PBS-treated control mice induced to develop experimental lung fibrosis. These findings demonstrate, 1) FAPL-S0456 can target the fibrotic lungs with good specificity, 2) targeted delivery of Pi3K inhibitor (FAPL-PI3KI1) may be beneficial in treating lung fibrosis, as well as other diseases that are characterized by pathological inflammation and fibrosis.

Various embodiments are provided to exemplify the making and using of FAP targeting conjugates and their promising effects on reducing or eliminating IPF symptoms, such as reduced collagen I production. Based on the expression pattern of FAP on various cancer tissues, it is contemplated that FAPL conjugated warhead can be used on other disease models as well, as long as the therapeutic drug conjugated to FAPL is specific and effective for the disease.

It is established that FAP protein expression is restricted, occurring at high levels on mesenchymal cells during embryogenesis then repressed shortly after birth, and its expression is upregulated on activated fibroblast in conditions associated with wound healing, cancer and fibrosis. From the examples below, a person skill in the art will appreciate that the expression pattern of FAP qualifies it as a good marker for the targeted delivery of drugs or other effectors to fibrotic cells, a hall mark of fibrosis.

Based on the data presented in the following examples, a FAP ligand targeted PI-3 kinase therapy can be primarily applied to adults at times when they are not recovering from a serious lung or other tissue trauma, one would not expect to encounter significant off target toxicity with the use of this drug.

It is also recognized that the fibrotic process share some similarities among different types of fibrosis, therefore, a targeted drug that might inactivate a myofibroblast and reprogram it to become a quiescence fibroblast might also prove useful in treating fibrosis of liver, kidney, heart, skin, and bladder organs. Without being restricted to any theory, this is because the basic pattern of disease progression in these several types of fibrosis may involve immune cell activation arising from unknown causes, leading to activation of fibroblasts to form myofibroblasts, thereby triggering the excessive production of collagen. Thus, a common feature in essentially all known fibrotic diseases is the production of collagen by the myofibroblasts, which invariably expresses FAP regardless of the organ in which the fibrosis occurs.

While a number of therapeutic warheads could have been selected for delivery with our FAP targeting ligand, for example, kinase inhibitors to VEGFR1, VEGFR2, VEDFR3, FGFR1, FGFR2, or PDGFR are potential candidates for delivery. Other warheads such as kinase inhibitors for FAK or ROCK, other effectors such as SMAD inhibitor, or cytotoxic agent, are all within the contemplation of this disclosure. In the instant application a potent pan PI-3 kinase inhibitor was selected in view of the many failures of prior PI-3 kinase inhibitors in the clinic, primarily due to its following advantages:

PI-3 kinase pathway activation is reported in fibrotic foci, the cardinal lesions in IPF. PI-3 Kinase isoforms exhibit increased expression in IPF tissue and fibroblast lines, with signaling activated downstream of several key profibrotic growth factors implicated in IPF, including platelet-derived growth factor and transforming growth factor (TGF)-β1. OMIPALISIB inhibited PI-3 Kinase signaling and functional responses in IPF-derived lung fibroblasts, inhibiting Akt phosphorylation in IPF lung tissue and BAL derived cells.

Inhibition of PI-3Kinase pathway also effects normal cellular functions, including proliferation, apoptosis and metabolism. A targeted approach is essential to prevent the cumulative toxicity of a pan-PI3K/mTOR inhibitor. Although an isoform-specific inhibitor could have been selected for delivery to the myofibroblasts, a pan-PI3K/mTOR kinase inhibitor was chosen to overcome any functional redundancy between isoforms and blocking potential crosstalk and feedback of compensatory mechanisms through inhibition of three key nodes (PI3K, mTORC1 and mTORC2).[25] While such a general PI-3 kinase inhibitor will generally be more toxic, suppressing all PI-3 kinase dependent processes is not so undesirable, since the myofibroblasts are not essential to normal lung function and they generally undergo apoptosis during resolution of the disease. It is interesting to note the specific accumulation of our FAPL-targeted fluorescent dye in the fibrotic lungs of the bleomycin-induced mice. Indeed, we have noted that the intensity of dye uptake correlates with the intensity of the fibrosis. In our studies of other targeting ligands developed for the treatment of other diseases, we have observed that the same targeting ligand can be used for delivery of a variety of useful payloads. If the same FAP-targeting ligand can be adapted for delivery of a radio-imaging agent to fibrotic tissues, the possibility exists that an FAP-targeted imaging agent might be developed for use in the diagnosis, staging or evaluation of response to therapy in IPF.

Last but not the least, due to PI-3 kinase's broad implications of different cell functions, particularly in some other disease models, it is contemplated that a given pan PI-3 kinase inhibitor war head can be conjugated to a targeting ligand to a specific disease marker, to exert its inhibitory effect in that particular disease model. For example, invasive bladder cancer treated with PI-3 kinase inhibitor can be improved with targeted ligand to bladder cancer marker Epidermal growth factor receptor (EPGR) conjugated with a choice of pan PI-3 kinase inhibitor. Our platform of pan PI-3 kinase warhead conjugated to a disease specific targeting ligand provides a therapeutic platform model for tackling various diseases that have unique surface marker expression on the diseased tissue.

Experimental Procedure

General. H-Cys(Trt)-2-Cl-Trt resin and protected amino acids were purchased from Chem-Impex Intl. 2-(Hydroxymethyl)pyridine-5-boronic acid, pinacol ester was purchased from Combi-Blocks. 6-bromo-4-iodoquinoline, 2-4-Diflurobenzene-1-sulfonyl-chloride and 5-bromo-2-methoxypyridine-3-amine was purchased from ArkPharm. All the other chemicals were purchased from SIGMA-Aldrich and Fisher Scientific and used as received. Thin layer chromatography (TLC) was carried out on Merck silica gel 60 F254 TLC plates. Silica gel column chromatography was performed using silica gel (60-120 µm particle size). Preparative reverse-phase high performance liquid chromatography (RP-HPLC) was performed on a Waters, XBridge™ Prep C18, 5 µm; 19×100 mm column, mobile phase A=20 mM ammonium acetate buffer, pH 5 or 7, B=acetonitrile, system with gradients in 30 min, 13 mL/min, λ=254/280 nm. The LRMS-ESI (LC-MS) was recorded on Agilent LCMS 1220 system, with Waters, XBridge™ RP18, 3.5 µm; 3×50 mm column, mobile phase A=20 mM ammonium bicarbonate buffer, pH 5 or 7, B=acetonitrile, system with gradients in 12-15 min, 0.75 mL/min, λ=254/280 nm. The high resolution mass measurements were recorded on a LTQ Orbitrap XL mass spectrometer utilizing electrospray ionization (ESI).

Synthesis

The FAP ligand (11), FAP-FITC and FAP-S0456 was synthesized following a previously published procedure. See WO2018111989A1.

Compound 3

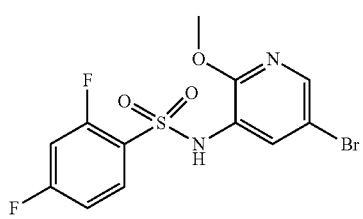

2-4-Diflurobenzene-1-sulfonyl-chloride 2 (1 eq) was added slowly to a cool solution of 5-bromo-2-methoxypyridine-3-amine 1 (1 eq) in pyridine. Reaction was stirred at ambient temperature for 16 h, at which time the reaction was diluted with water and the solids were filtered off and washed with copious amounts of water. The precipitate was dried in high vacuum to give compound 3, and was used in the next step without further purification. LRMS-LC/MS (m/z): [M+H]$^+$ calcd for $C_{12}H_9BrF_2N_2O_3S$, 377.9; found 378.9).

Compound 5

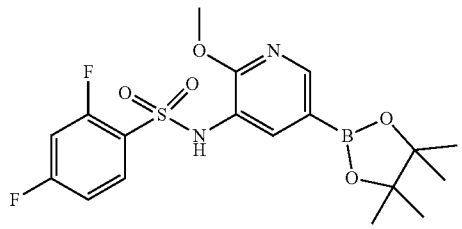

A mixture of Bis(Pinacolato)diboron 4 (1 eq), compound 3 (1 eq), Pd(dppf)$_2$Cl$_2$ (0.1 eq), KOAc (3 eq) in anhydrous 1,4-dioxane was deoxygenated by bubbling nitrogen through it for 10 min. The mixture was then heated at reflux for 3 h. After cooling to room temperature, the mixture was evaporated under reduced pressure and the residue was dissolved in EtOAc, washed with water twice and dried over magnesium sulfate. The crude product was purified by flash chromatography (Hex: EtOAc) to give compound 5. LRMS-LC/MS (m/z): [M+H]$^+$ calcd for $C_{18}H_{21}BF_2N_2O_5S$, 426.1; found 427.1).

Compound 8

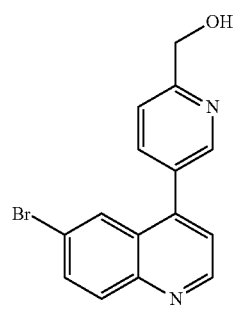

6-bromo-4-iodoquinoline 6 (212.37, 0.636 mmol) and 2-(Hydroxymethyl)pyridine-5-boronic acid 7 (150 mg, 0.636 mmol) was dissolved in anhydrous 1,4-dioxane (15 mL). To this was added Pd(dppf)$_2$Cl$_2$ (19.9 mg, 0.024 mmol) followed by 2M Na$_2$CO$_3$ (2.5 mL). The mixture was then heated at reflux for 6 hrs. After cooling to room temperature the solids were filtered off and evaporated. The crude product was purified by flash chromatography (EtOAc: MeOH) to give compound 8. LRMS-LC/MS (m/z): [M+H]$^+$ calcd for $C_{15}H_{11}BrN_2O$, 314; found 315).

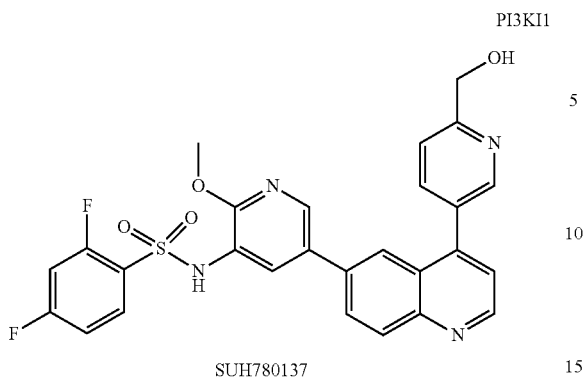

PI3KI1

SUH780137

Compound 5 (136 mg, 0.32 mmol) and compound 8 (110 mg, 0.32 mmol) was dissolved in anhydrous 1,4-dioxane (50 mL). To this was added Pd(dppf)$_2$Cl$_2$ (10 mg, 0.012 mmol) followed by 2M Na$_2$CO$_3$ (8 mL). The mixture was then heated at reflux for 6 hrs. After acooling to room temperature the solids were filtered off and the residue evaporated. The crude product was purified by flash chromatography (EtOAc:MeOH) to give PI3KI1. LRMS-LC/MS (m/z): [M+H]$^+$ calcd for C$_{27}$H$_{20}$F$_2$N$_4$O$_4$S, 534.1; found 535.1)

Compound 10

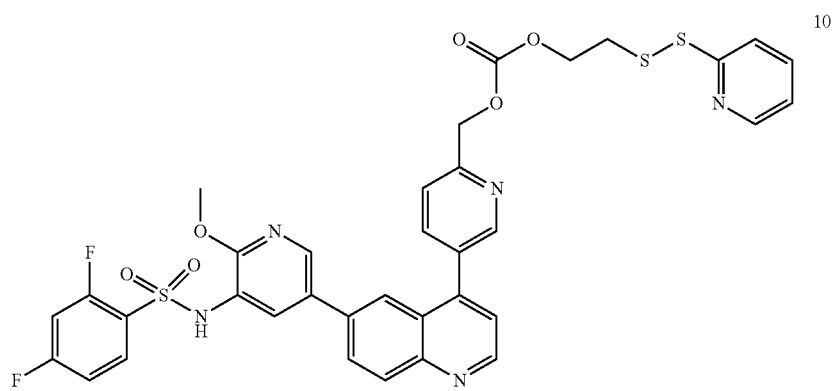

SUH78017 (50 mg, 0.094 mmol) and compound 9 (32.7 mg, 0.094 mmol) was dissolved in DMF (1 mL) and stirred. Progress of the reaction was monitored by analytical LRMS-LCMS. Following the completion of the reaction crude product was purified by preparative RP-HPLC [A=2 mM ammonium acetate buffer (pH 7.0), B=acetonitrile, solvent gradient 5% B to 80% B in 35 min] to yield 80% of compound 10. LRMS-LC/MS (m/z): [M+H]$^+$ calcd for C$_{35}$H$_{27}$F$_2$N$_5$O$_6$S$_3$, 747.1; found 748.1)

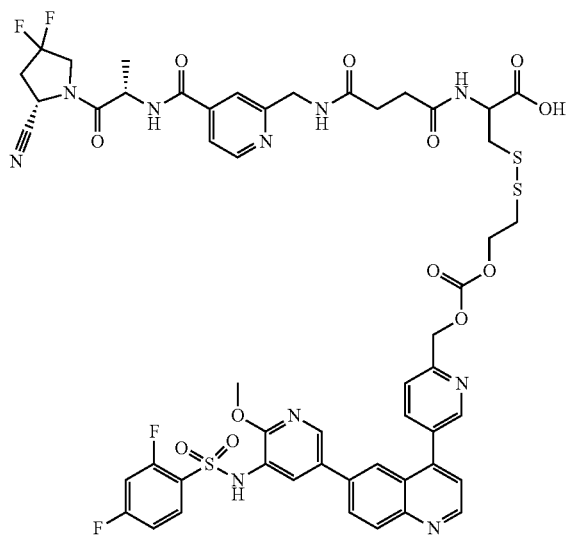 [SMILES: COc1ncc(-c2ccc3nccc(-c4ccc(COC(=O)OCCSSCC(NC(=O)CCC(=O)NCc5cc(C(=O)N[C@@H](C)C(=O)N6CC(F)(F)C[C@H]6C#N)ccn5)C(=O)O)nc4)c3c2)cc1NS(=O)(=O)c1ccc(F)cc1F]

FAP-PI3KI1

Compound 10 (22.3 mg, 0.019) and compound 11 (10 mg, 0.018 mmol) was dissolved in anhydrousDMSO and stirred under inert atmosphere. Progress of the reaction was monitored by analytical LRMS-LCMS. Following the completion of the reaction crude product was purified by preparative RP-HPLC [A=2 mM ammonium acetate buffer (pH 7.0), B=acetonitrile, solvent gradient 5% B to 80% B in 35 min] to yield 80% of the final product FAP-PI3KI1. LRMS-LC/MS (m/z): $[M+H]^+$ calcd for $C_{52}H_{48}F_4N_{10}O_{12}S_3$, 1177.2 found 1179.1).

Cell Culture and Animal Husbandry

IPF patient cell lines were kindly donated by Dr. Ivan O. Rosas, M.D. Brigham and Women's Hospital, Boston, MA. C57BL6/6-NCrl (Strain code: 027) mice were purchased from Charles River and maintained on normal rodent chow. They were housed in a sterile environment on a standard 12 h light-and-dark cycle for the duration of the study. All animal procedures were approved by the Purdue Animal Care and Use Committee (PACUC) in accordance with NIH guidelines.

In Vitro Studies

Live Cell Imaging of FAP-FITC Internalization

HLF1-hFAP cells were seeded in the glass-bottom dish and incubated with adequate amount of endosomes tracker (Rab7a-RFP, ThermoFisher) for overnight. Then cells were incubated with FAP-FITC (10 nM) for 1 hour at 4° C. Followed by staining with 5 nM DRAQ5 nucleus dye (ThermoFisher) and 3 times of PBS washes, spatial localization of FAP-FITC was monitor at given time under ambient temperature by confocal microscope (FV 1000, Olympus). Confocal images were further processed by FV10-ASW, Olympus software.

Immunofluorescence of FAP and αSMA Expression in Fibroblasts

HLF1 cells, primary IPF fibroblasts and the non-IPF fibroblasts were cultured, fixed, and permeabilized on glass-bottom dishes for immunofluorescent staining. Primary antibodies against hFAP (1:200, FAB3715R, R&D Systems) or αSMA (1:1000, ab21027, Abcam) were incubated overnight at 4° C. After PBS washes, incubated with secondary antibody of Alexa Fluor® 488 anti-Goat antibodies (Abcam, 1:400). Images were captured and analyzed by confocal microscope.

Sirius Red Staining for Secreted Total Collagen

Confluent HLF1 cells were seeded in DMEM medium containing 10% FBS and then 0.4% serum starvation overnight before stimulation of collagen secretion. TGFb1 (0.1 ng/ml) were added into cells with or without PI3K inhibitors. At 2 days post co-incubation, culture medium was collected for determination of total secreted collagen level. Total collagen level was determined by Sirius Red Total Collagen Detection Kit (Chondrex, Inc). Basically, concentrated sample incubated with 500 ml of Sirius Red Solution with for 20 minutes at room temperature. Pellet was collect by centrifuge at 10,000 rpm for 3 minutes and followed by washing with 500 ml of washing solution for 3 times. Add 250 ml of Extraction Buffer to the Sirius Red stained pellet and read the OD at 510-550 nm.

Western Blot Analysis of Cultured Fibroblasts

Serum starved confluent HLF1 cells were co-incubated in medium containing 1 ng/ml TGFb1 with or without designate concentrations of PI3K inhibitors for 24 hours. Cells were harvested and lysed for Western blot analysis. Following sodium dodecyl sulphate polyacrylamide gel electrophoresis and blocking, membranes were incubated with antibodies to detect $pSMAD2^{Ser465/467}$ (#3101, Cell Signalling Technology), or $pAkt^{Ser473}$ (#4060, Cell signalling Technology), and signals visualized with ECL Western Blotting Detection Reagents (GE Healthcare). Following stripping, membranes were blocked and re-probed with antibodies specific for total SMAD2 (#3103, Cell Signalling Technology) or total Akt (#4060, Cell Signalling Technology).

In Vivo Studies

Bleomycin-induced Lung Fibrosis Model 8 to 10-week old C57BL/6-NCrl (Strain Code: 027) male mice (Charles River) were anesthetized (mixture of xylazine/ketamine), followed by a single intratracheal injection of freshly prepared 0.75 mg/Kg of bleomycin sulfate (Cayman Chemicals, Cat N13877) in 50 □L of sterile phosphate-buffered saline (PBS). Control mice were injected with 50 □L of sterile PBS. Body weights were monitored throughout the study. To access the FAP expression and fibrosis in the longitudinal study the lungs were harvested at Days 7, 14 and 21 post-bleomycin instillation. For the therapy with FAP-PI3K inhibitor, same procedure was carried out to administer bleomycin and the lungs were harvested at Day 21 to access the therapeutic efficacy (Day 0 was accounted as the day of bleomycin administration).

Hydroxyproline Assay

Total lung collagen was determined by analysis of hydroxyproline as previously described.[30] The right lung was consistently dedicated for this assay to allow comparison. Briefly, harvested right lung was homogenized in PBS (PH 7.4), digested with 12N HCl at 120° C. for 3 hr. Citrate/acetate buffer (PH 6.0) and Chloramine-T solution were added at room temperature for 20 minutes and the samples were incubated with Ehrlich's solution for 15 min at 65° C. Samples were cooled to room temperature and read at 550 nm. Hydroxyproline standards (Sigma, MO) at concentrations between 0 to 100 μg/ml were used to construct a standard curve.

Histopathological Evaluation of Pulmonary Fibrosis

The left lung was inflated and fixed with 4% paraformaldehyde. Lung tissues were embedded in paraffin, and 10-μm sections were prepared and stained using H&E and Masson's Trichrome. The severity of bleomycin-induced fibrosis was determined by semiquantitative histopathological scoring, at the indicated dates after bleomycin administration.[29]

In Vivo Fluorescence Imaging

Mice were treated via tail vein (i.v.) injection with 5 nmol of FAP targeted NIR dye conjugate (FAP-S0456) and imaged 2 hr post-injection using a Spectral AMI optical imaging system. For competition experiments, a 100-fold excess of base the FAP ligand was used. The settings were as follows: Object height, 1.5; excitation, 745 nm; emission, 790 nm; FOV, 25; binning, 2; f-stop, 2; acquisition time, 1 s. After the completion of whole-body imaging, animals were dissected, and selected organs were collected and imaged again for complete biodistribution. The conditions remained same for the longitudinal imaging study, except the mice were imaged at day 7, day 14, and day 21 post-bleomycin administration.

In Vivo Micro-CT Imaging

Micro-CT analysis of the whole lung was performed at day 7, day 14, and day 21 post-bleomycin administration Briefly animals were anesthetized with isoflurane and fixed in prone position. Micro-CT images were acquired on a Quantum FX micro-CT system (Perkin Elmer, Waltham, MA) with cardiac gating (without respiratory gating), using the following parameters: 90 kV; 160 μA; FOV, 60×60×60 mm; spatial resolution, 0.11 mm, resulting in a total acquisition time of 4-5 minutes

EXAMPLE 1. DESIGN AND SYNTHESIS OF FAPL-FITC CONJUGATE FOR ANALYSIS OF FAP TARGETING

Figure 1:
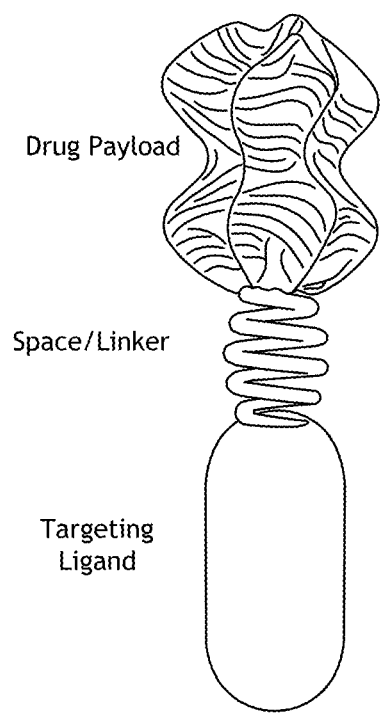
FIG. 1. Design and Synthesis of FAPL-FITC conjugate for analysis of FAP targeting.
Figure 1:
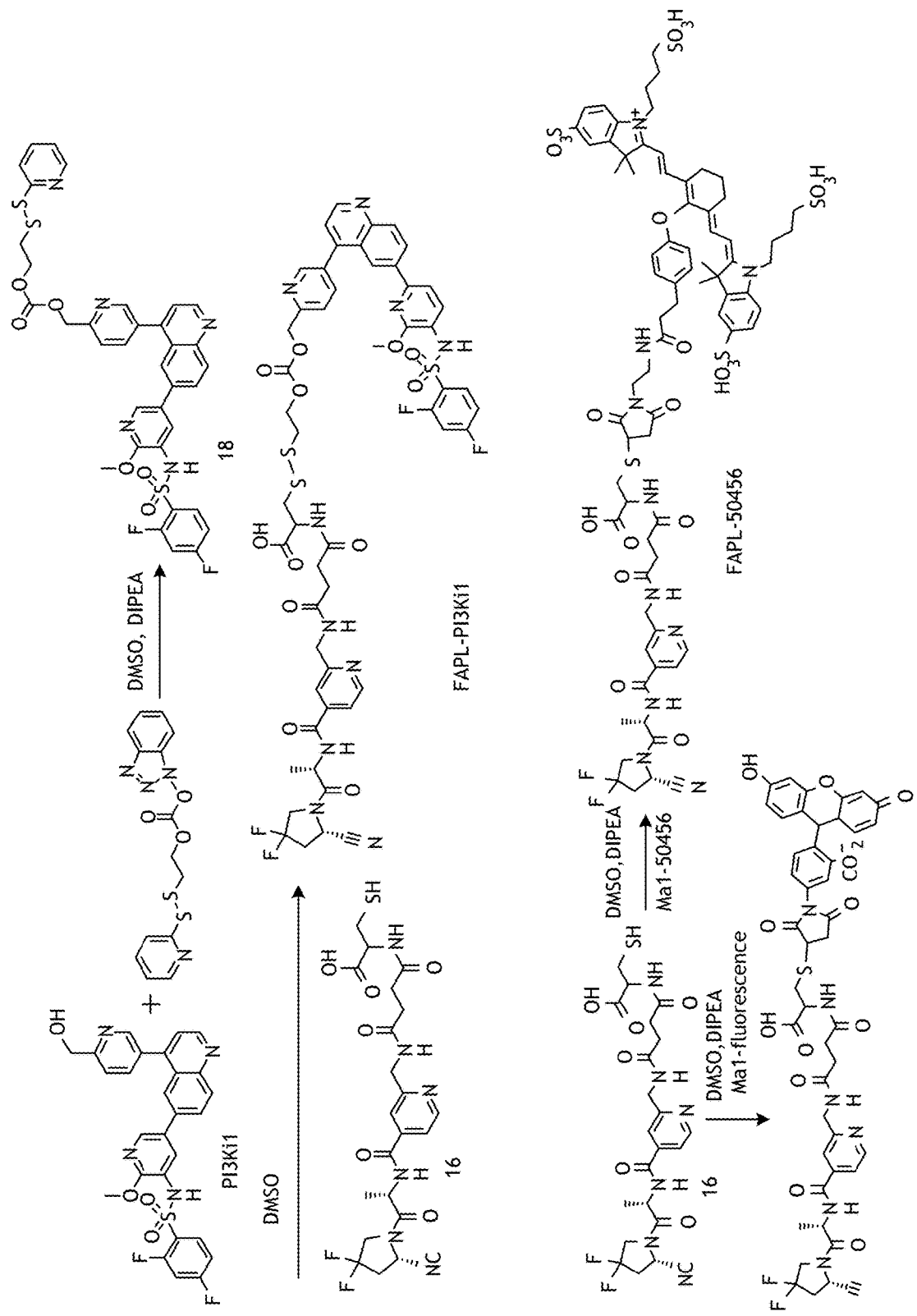

In this Example, an imaging agent conjugate comprising FAP targeting ligand (FAPL) and a fluorescein such as FITC was generated according to the scheme shown in FIG. 1.

Figure 2:
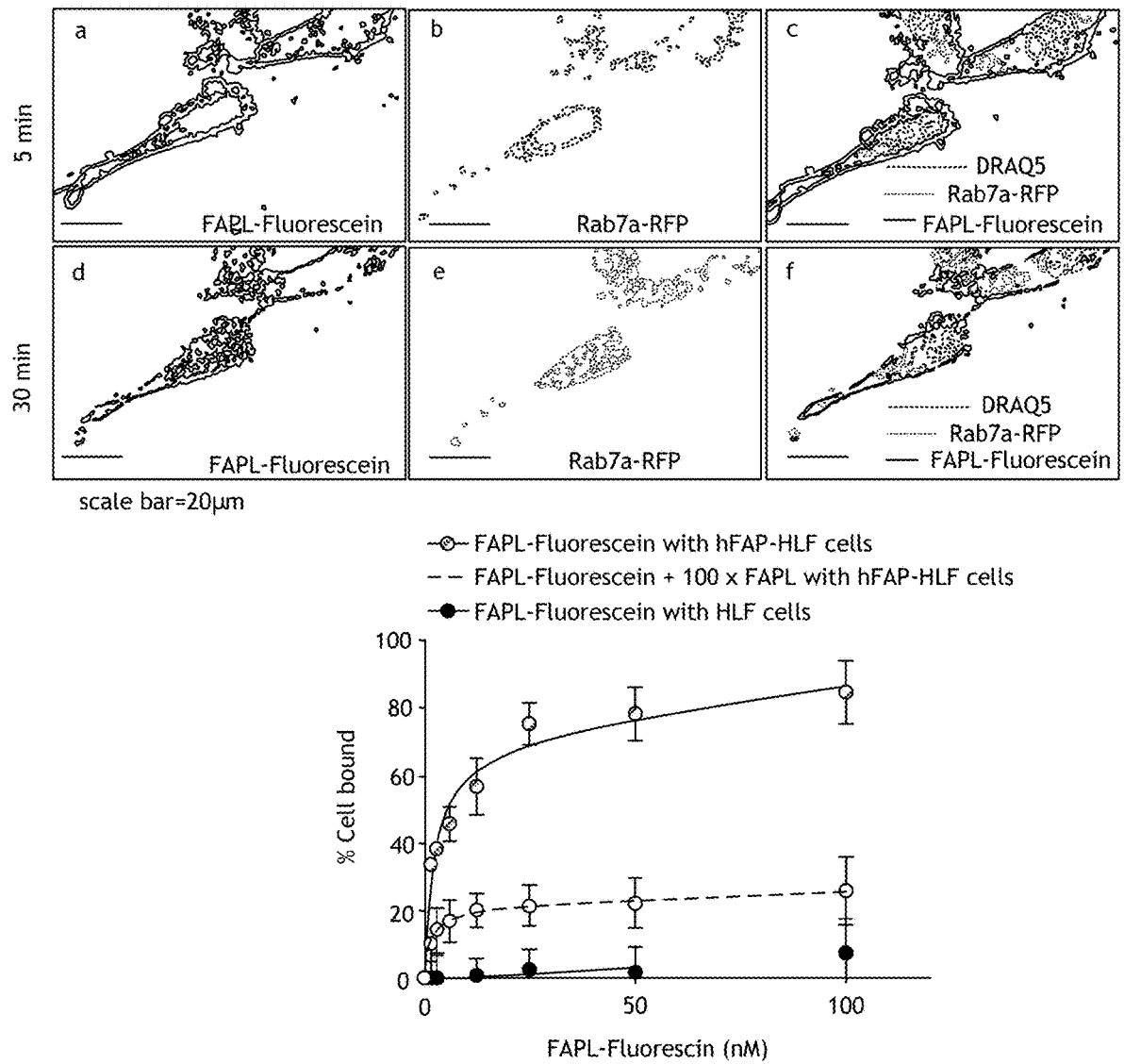
FIG. 2. Binding and internalization of FAPL-FITC by human fibroblast cell line FAPL-FITC targets human FAP in HLF1 cells. A) Live cell imaging of FAPL-FITC internalization. confocal microscopy images of HLF1-hFAP cells incubated with FAPL-FITC (10 nM), FAP staining is shown in green. Spatial localization of FAPL-FITC in HLF1-hFAP cell line at 0 min (a), and at 30 min (d). Colocalization of FAP and endosomes: HLF1-hFAP cells incubated with FAPL-FITC followed by staining for endosomes (Rab7a-RFP; red) and nucleus (DRAQ5; blue). The merge of the 3 images is shown on the right (c, and f). Yellow indicated colocalization of FAP with endosomal markers.

In order to determine the conjugate's in vitro binding features such as binding affinity to FAP, and its bio distribution within FAP expressing cells, FAPL-FITC conjugate was incubated with a FAP transfected cell line HLF1 (human fibroblast cells), confocal microscopy and flow cytometry are used to observe the conjugate's specific targeting to FAP expressing cell line, and its subsequent endocytosis in the cell line. See FIG. 2 and its legend, which shows FAPL-FITC binds well with good competition in the hFAP-HLF1 cell line. In addition, FAP ligand can recognize and target FAP with good specificity. FAPL_FITC conjugates are internalized upon receptor engagement. This shows the conjugate is likely to deliver a payload of effectors to the activated fibroblast, for example, the imaging agent or, a therapeutic drug.

EXAMPLE 2. BINDING OF FAPL-FITC BY HUMAN IPF PATIENT CELL LINE

Figure 3A:
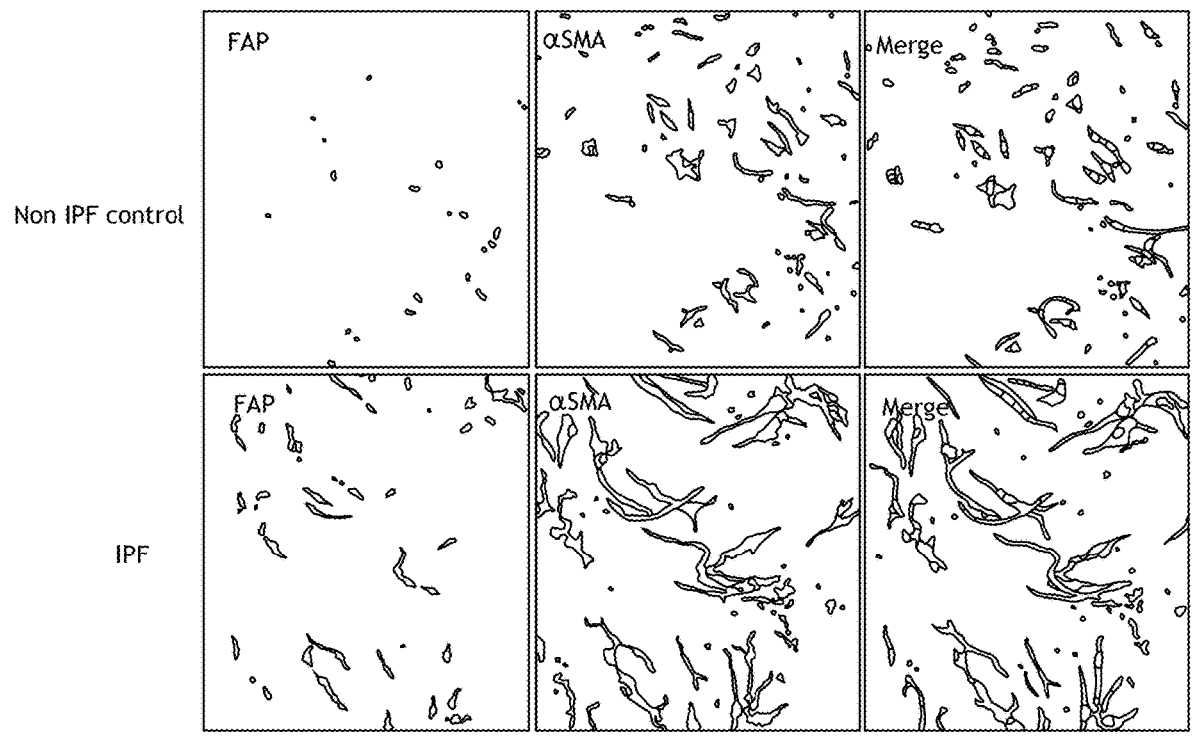
FIG. 3. Binding of FAPL-FITC by human IPF patient cell line
Figure 3B:
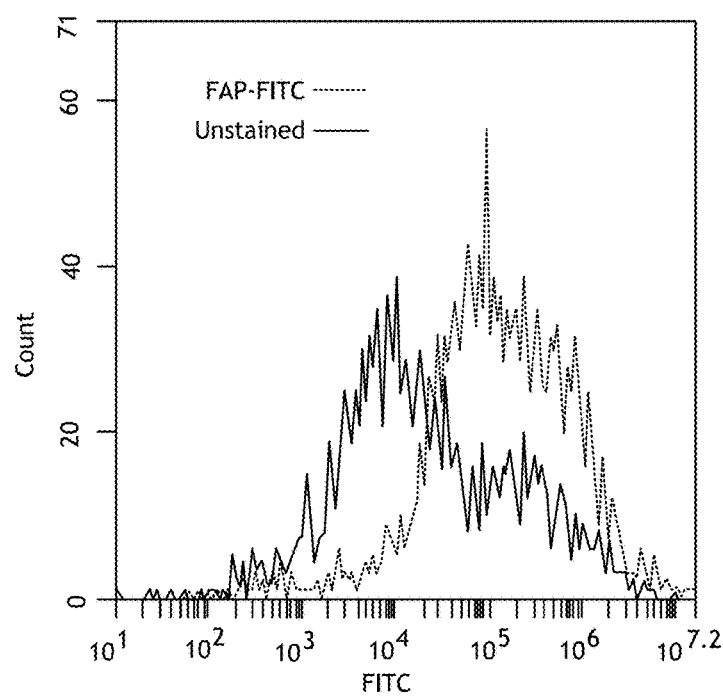

In this Example, human IPF patient cell line and non-IPF control cell line were stained with FAP antibody and aSMA antibody respectively. Confocal microscopy indicates both FAP and aSMA are predominantly expressed in IPF lung fibroblasts. See FIG. 3A. When the IPF patient cell line is incubated with FAPL_FITC, the flow cytometry analysis shows FAPL_FITC stained samples in FIG. 3B.

EXAMPLE 3. DESIGN, SYNTHESIS OF PI3KI1 AND FAP-PI3KI1

In this Example, we provided a novel pan PI-3Kinase-mTOR inhibitor named PI3KI1. This potential IPF drug has a good handle to incorporate releasable linkers to conjugate to a targeting ligand, for example, a FAP ligand in example 2-3.

The design and synthesis of the novel pan PI-3Kinase-mTOR inhibitor is shown in FIG. 4.

The synthesis scheme of novel FAP targeted pan-Pi3K inhibitor (FAPL PI3KI1) is shown in FIG. 5.

EXAMPLE 4. EVALUATION OF MYOFIBROBLAST INACTIVATION WITH FAPL-TARGETED PI-3 KINASE INHIBITOR IN VITRO

In this Example, we have shown that the novel PI-3Kinase inhibitor PI3KI1 inhibits Akt phosphorylation better than its GSK counterpart OMIPALISIB. The latter is in a clinical trial for IPF therapeutic drug. The PI3KI1 also suppresses collagen secretion and collagen gel contraction in HLF-1 cell line. Because the novel PI-3Kinase inhibitor PI3KI1 has a free hydroxyl group, it allows facile conjugation to a FAP ligand, show in the example 2 and 3. The novel drug does not have toxicity and it behaves similarly to GSK drug OMIPALISIB. See FIG. 6 and its Legend.

EXAMPLE 5. EX VIVO IPF PATIENT CELL LINE DATA

In this Example we established that FAP targeted PI-3 kinase inhibitor FAP_PI3KI1 suppresses TGFβ induced collagen secretion at low drug concentration, better than free PI3KI1 and free GSK drug OMIPALISIB in IPF patient cells. See FIG. 7 and its legend.

EXAMPLE 6. EVALUATION OF FAP TARGETING IN MOUSE FIBROBLAST CELL LINE IN VITRO

In this Example, we have shown that FAPL_FITC can recognize mouse FAP. Briefly, NIH-3T3 cells were induced with TGFβ to express FAP (mimicking the pathogenesis of fibrosis in mice). FAPL_FITC can recognize almost 98% of the cell population that binds to a specific monoclonal antibody against mouse FAP. See FIG. 8 and its legends.

EXAMPLE 7. EVALUATION OF FAP TARGETING OF IPF LUNG IN MOUSE MODEL OF IPF IN VIVO

In this Example, FAPL conjugated with drug or other effector specifically target fibrotic lungs in mice day 14 after acute lung injury. Briefly, both the saline treated and fibrotic lungs with FAP competition showed minimum retention of the NIR signal while the diseased lung without competition showed high uptake of the FAP_S0456 dye. Both micro CT and NIR imaging at different time points (day 7, 14, 21) after acute lung injury, showed progression of fibrosis.

In correlation with the hydroxyproline and immunostaining data, it is shown that highest optical intensity was achieved at day 14, indicating peak fibrosis, and slowly subside around day 21. See FIG. 9 and its legends.

EXAMPLE 8. EVALUATION OF MYOFIBROBLAST INACTIVATION WITH FAPL-TARGETED PI-3 KINASE INHIBITOR IN VIVO

In this Example, attenuation of fibrosis was demonstrated with the increased survival rate, and the reduction of hydroxyproline in the FAPL_PI3KI-SUH treated mice over the untreated mice. See FIG. 10 and its legends.

EXAMPLE 9. IMAGING DISTRIBUTION OF LUNG FIBROSIS

In this example, Radio-imaging of experimental lung fibrosis is shown in FIG. 19A (in various organs) and in FAP target $^{99m}$TC in the lungs (FIG. 19B).

The invention claimed is:

1. A PI-3 kinase inhibitor represented by the formula:

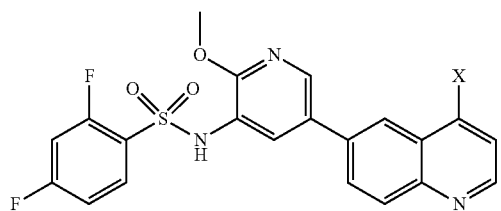

wherein X is selected from the group consisting of:

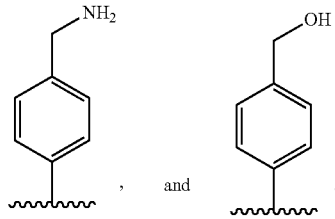

2. A conjugate comprising:
i) a FAP-binding ligand (TL);
ii) a linker (L); and
iii) a radical of a PI-3 kinase inhibitor (E) represented by the formula:

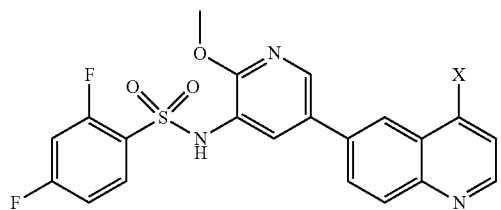

wherein X is selected from the group consisting of:

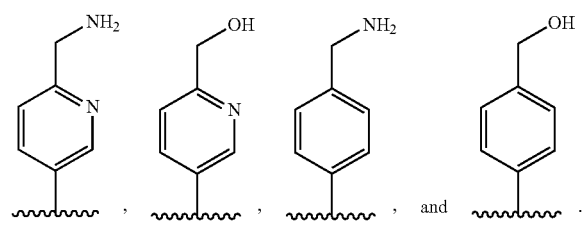 [SMILES: *c1ccc(CN)nc1 ; *c1ccc(CO)nc1 ; *c1ccc(CN)cc1 ; *c1ccc(CO)cc1]

3. The conjugate of claim 2, wherein TL is represented by the formula:

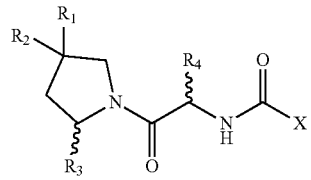

wherein:

X is:

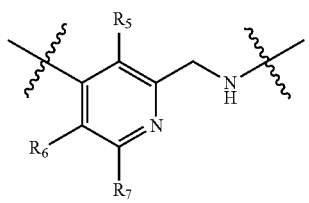

or

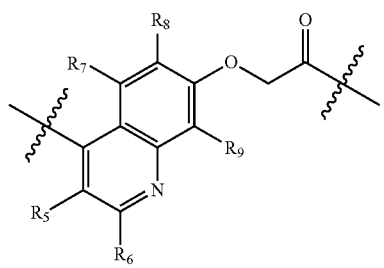

$R_1$ and $R_2$ are the same or different, and are each independently selected from the group consisting of hydrogen, halogen and $C_1$-$C_4$ alkyl;

$R_3$ is $C_1$-$C_4$ alkyl, nitrile, or isonitrile;

$R_4$ is H or —$CH_3$;

$R_5$ and $R_6$ are the same or different, and are each independently selected from the group consisting of hydrogen, halogen, and C1-C4 alkyl, and $R_7$, $R_8$, and $R_9$ are the same or different, and are each independently selected from the group consisting of hydrogen, methoxy, halogen, —$CF_3$ and $C_1$-$C_4$ alkyl.

4. The conjugate of claim 2, wherein TL has a binding affinity to FAP in the range between about 1 nM and about 20 nM.

5. The conjugate of claim 2, wherein TL has a molecular weight below 10,000 Da.

6. The conjugate of claim 2, wherein L is selected from the group consisting of a polyethylene glycol (PEG), an alkyl, a sugar, and a peptide.

7. The conjugate of claim 2, wherein L is a releasable linker.

8. The conjugate of claim 6, wherein the linker is a PEG.

9. A pharmaceutical composition comprising the conjugate of claim 2 and a pharmaceutically acceptable excipient.

10. A compound comprising the formula:
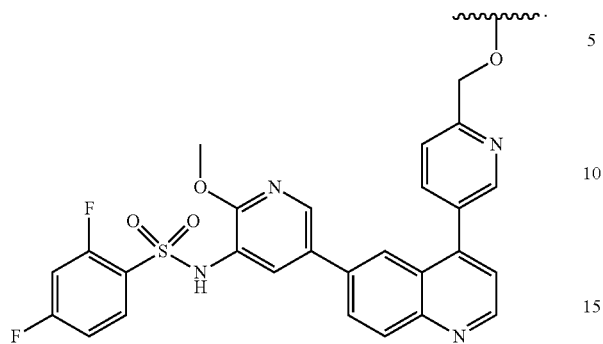
11. A pharmaceutical composition comprising the compound of claim 10 and a pharmaceutically acceptable excipient.
* * * * *

UNITED STATES PATENT AND TRADEMARK OFFICE
CERTIFICATE OF CORRECTION

PATENT NO. : 11,890,357 B2
APPLICATION NO. : 17/809810
DATED : February 6, 2024
INVENTOR(S) : Low et al.

It is certified that error appears in the above-identified patent and that said Letters Patent is hereby corrected as shown below:

In the Claims

In Column 25, Lines 26-35, in Claim 1, delete "  " and insert --  -- therefor In Column 26, Line 48, in Claim 3, delete "C1-C4" and insert --$C_1$-$C_4$-- therefor Signed and Sealed this
Eighth Day of April, 2025

Coke Morgan Stewart
*Acting Director of the United States Patent and Trademark Office*